United States Patent
Boon et al.

(10) Patent No.: US 8,603,518 B2
(45) Date of Patent: Dec. 10, 2013

(54) HYDROXYBUTYRATE AND POLY-HYDROXYBUTYRATE AS COMPONENTS OF ANIMAL FEED OR FEED ADDITIVES

(75) Inventors: Nico Boon, Balegem (BE); Tom Defoirdt, Anzegem (BE); Wim De Windt, Sint-Amandsberg (BE); Tom Van De Wiele, Boltelare (BE); Willy Verstraete, Wondelgem (BE)

(73) Assignee: Universiteit Gent, Ghent (BE)

( * ) Notice: Subject to any disclaimer, the term of this patent is extended or adjusted under 35 U.S.C. 154(b) by 1035 days.

(21) Appl. No.: 12/299,182

(22) PCT Filed: May 1, 2007

(86) PCT No.: PCT/EP2007/003835
§ 371 (c)(1),
(2), (4) Date: Dec. 9, 2009

(87) PCT Pub. No.: WO2007/124949
PCT Pub. Date: Nov. 8, 2007

(65) Prior Publication Data
US 2010/0093860 A1    Apr. 15, 2010

Related U.S. Application Data

(60) Provisional application No. 60/796,436, filed on May 1, 2006.

(30) Foreign Application Priority Data

May 9, 2006 (EP) .................................... 06009515
Feb. 23, 2007 (EP) .................................... 07003803

(51) Int. Cl.
*A23K 1/17* (2006.01)
*A23K 1/165* (2006.01)

(52) U.S. Cl.
USPC ...................................................... 424/442

(58) Field of Classification Search
USPC .......................................................... 424/442
See application file for complete search history.

(56) References Cited

U.S. PATENT DOCUMENTS 5,461,073 A    10/1995  Katayama
6,207,217 B1 *  3/2001  Peoples et al. ................. 426/635
(Continued)

FOREIGN PATENT DOCUMENTS

| DE | 102 12 553 | * | 9/2003 |
| EP | 1 661 574 | | 5/2006 |
| WO | WO 2005/021013 | | 3/2005 |
| WO | WO 2005/056002 | | 6/2005 |

OTHER PUBLICATIONS

The English abstract of DE 102 12 553.*
(Continued)

*Primary Examiner* — San-Ming Hui
(74) *Attorney, Agent, or Firm* — Clark & Elbing LLP

(57) ABSTRACT

This invention relates to the use of hydroxybutyrate and poly hydroxybutyrate as components of animal feed or feed additives, as well as to compositions, feed additives and feed containing them. The inventors surprisingly found that hydroxybutyrate and poly-hydroxybutyrate, preferably 3-hydroxybutyrate and poly-3-hydroxybutyrate, have a great potential for use in animal feed for modulation of the gut flora. More precisely, it has been found that poly-3-hydroxybutyrate or a microbial strain capable for producing poly-3-hydroxybutyrate can be used as a potential growth promoter or gut flora modulator by releasing SCFA, preferably 3-hydroxy butyric acid, in the gut micro flora. Further, the inventors found that 3-hydroxybutyrate and poly-3-hydroxybutyrate have a great potential for suppressing or inhibiting pathogenic bacteria in the gastro intestinal tract, e.g. have a antimicrobial activity against strains of *Vibrio*, *E. coli* and *Salmonella*.

14 Claims, 4 Drawing Sheets

(56) References Cited

U.S. PATENT DOCUMENTS

2002/0077334 A1 6/2002 Cook et al.
2004/0220093 A1 11/2004 Stern et al.
2006/0210630 A1 9/2006 Liang et al.
2006/0275253 A1 12/2006 Ushida et al.

OTHER PUBLICATIONS

Summons to Attend Oral Proceedings Pursuant to Rule 115(1) EPC issued in European Patent Application No. 07724762.5, dated Nov. 15, 2012 (5 pages).
International Preliminary Report on Patentability for International Application PCT/EP2007/003835, mailed Nov. 13, 2008.
Office Communication for Australian Patent Application No. 2007245806, dated Nov. 1, 2011.
Office Action for European Patent Application No. 07 724 762.5, dated May 5, 2010.
Cook et al., "Review Article: Short Chain Fatty Acids in Health and Disease," *Alimentary Pharmacology & Therapeutics*, 12: 499-507, 1998.
English Translation of WO 2005/021013, 2005.
International Search Report and Written Opinion (PCT/EP2007/003835) mailed Aug. 7, 2007.

\* cited by examiner

HYDROXYBUTYRATE AND POLY-HYDROXYBUTYRATE AS COMPONENTS OF ANIMAL FEED OR FEED ADDITIVES

CROSS-REFERENCE TO RELATED APPLICATIONS

This application is the U.S. National Stage of International Application No. PCT/EP2007/003835, filed May 1, 2007, which, in turn, claims the benefit of U.S. Provisional Application No. 60/796,436, filed May 1, 2006, European Patent Application No. 06009515.5, filed May 9, 2006, and European Patent Application No. 07003803.9, filed Feb. 23, 2007.

BACKGROUND OF THE INVENTION

This invention relates to the use of hydroxybutyrate and poly-hydroxybutyrate as components of animal feed or drinking water or feed or drinking water additives, as well as to compositions, feed additives, drinking water and feed containing them.

The term feed or feed composition means any compound, preparation, mixture, or composition suitable for, or intended for intake by an animal.

More particular, the present invention relates to the use of 3-hydroxybutyrate (HB) or a salt, ester, or combination of HB, a HB salt and a HB ester, or poly-3-hydroxybutyrate (PHB) or a salt, ester, or combination of PHB, a PHB salt and a PHB ester as active ingredients of nutraceutical compositions for animals.

The term "nutraceutical" as used herein denotes a usefulness in both the nutritional and pharmaceutical field of application. Thus, the nutraceutical compositions can find use as a complete animal feed (diet), as supplement to animal feed, and as pharmaceutical formulations for enteral or parenteral application which may be solid formulations, or liquid formulations.

The term animal includes all animals including human. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

In farm animals suppression of enteric diseases on one hand and growth promotion on the other hand have been achieved by the inclusion of antibiotics and/or chemotherapeutics into the diets.

On the one hand, butyric acid is known as a "soft" antimicrobial which shows a "prebiotic" effect when treated to animals. Butyric acid has a strong positive effect on the enterocytes and colonocytes proliferation and maturation. Currently butyric acid is added (mostly together with antibiotics) to animal feed as prebioticum after it is synthesized, neutralized with CaO and worked up with silicate. But one of the big disadvantages of using butyric acid in animal nutrition is that the current butyric acid products are sticky and smell very bad.

On the other hand, in recent years, considerable attention has been also paid to short chain fatty acids (SCFAs) as an alternative to traditional growth promoters. For example European patent application 1'661'574 discloses a composition comprising polymers of short to medium chain hydroxy fatty acids, hereinafter also called "Polyhydroxyalkanoates (PHAs)", which are used for delivering the hydroxy fatty acid or an oligomer thereof to the large intestine. In case the composition is administrated orally, the composition will be delivered to the large intestine, without being degraded in the stomach or short intestine, but being degraded by the large intestinal bacterial flora resulting in the release of the short to medium chain fatty acids or oligomers thereof. EP 1'661'574 further discloses that the released short to medium chain fatty acids or oligomers thereof have useful physiological activities and are effective for treating or preventing inflammatory diseases or cancer in the large intestine.

SUMMARY OF THE INVENTION

The present inventors now surprisingly found that hydroxybutyrate and poly-hydroxybutyrate, preferably 3-hydroxybutyrate and poly-3-hydroxybutyrate, have a great potential for use in animal feed or drinking water for modulation of the gut flora. More precisely, it has been found that poly-3-hydroxybutyrate or a probiotic strain capable of producing poly-3-hydroxybutyrate can be used as a potential growth promoter or gut flora modulator by releasing SCFA, preferably 3-hydroxy butyric acid, already in the small intestine. Further, the inventors found that 3-hydroxybutyrate and poly-3-hydroxybutyrate have a great potential for suppressing or inhibiting pathogenic bacteria, e.g. have antimicrobial activity against strains of *E. coli, Salmonella* and *Vibrio*.

As described above, feeding PHB to higher organisms allows liberation of butyric acid in the gastrointestinal tract. This feeding results in an attractive bacteriostatic effect, comparable with butyric acid currently added to animal feed as prebioticum. Furthermore, PHB is much better formulated doesn't smell and can be added as small particles in the animal feed.

Feeding PHB to higher organisms according to the present invention further allows a constant, preferably slow and controlled release of the active SCFA monomers in the gastrointestinal tract.

The closest prior art document EP-A-1'661'574 is silent on the use of hydroxy-butyric acid or of poly-hydroxybutyrate for addition to feed or drinking water to modulate the gut microflora and on the use of these compounds as antimicrobial agents against *Vibrio, Salmonella, Escherichia coli* and other pathogenic micro-organisms.

Therefore in a first object, the present invention relates to the use of hydroxybutyrate and/or poly-hydroxybutyrate, preferably 3-hydroxybutyrate and/or poly-3-hydroxybutyrate, and strains of microorganisms, which produce hydroxybutyrate and/or poly-hydroxybutyrate, preferably 3-hydroxybutyrate and/or poly-3-hydroxybutyrate in animal feed for modulation of the gut micro flora. Accordingly, the present invention provides methods for modulating the gut microflora of an animal, which method comprises the step of administering to the animal an animal feed comprising hydroxybutyrate and/or poly-hydroxybutyrate, preferably 3-hydroxybutyrate and/or poly-3-hydroxybutyrate and/or comprising strains of microorganisms, which produce hydroxybutyrate and/or poly-hydroxybutyrate, preferably 3-hydroxybutyrate and/or poly-3-hydroxybutyrate.

The term "gut" as used herein designates the gastrointestinal or digestive tract (also referred to as the alimentary canal) and it refers to the system of organs within multicellular animals, which takes in food, digests it to extract energy and nutrients, and expels the remaining waste. In particular embodiments, the term "gut" encompasses the stomach, small intestine and large intestine. The "upper gut" as used herein refers to the gut excluding the large intestine.

The term gut "microflora", alternatively specified as gut "microbiota", as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use. The modulation is in response to PHB's of the invention.

BRIEF DESCRIPTION OF THE DRAWINGS

FIG. 3 is a series of graphs showing viable counts of *Salmonella* and coliform bacteria in colon suspensions. FIG. 4 is a graph showing that supplementation with 3HB results in a significant increase of butyrate and acetate levels. FIG. 5 is a graph showing a decrease in 3HB concentration corresponding with an equivalent increase of acetate and butyrate levels.

DETAILED DESCRIPTION OF THE INVENTION

Figure 1:
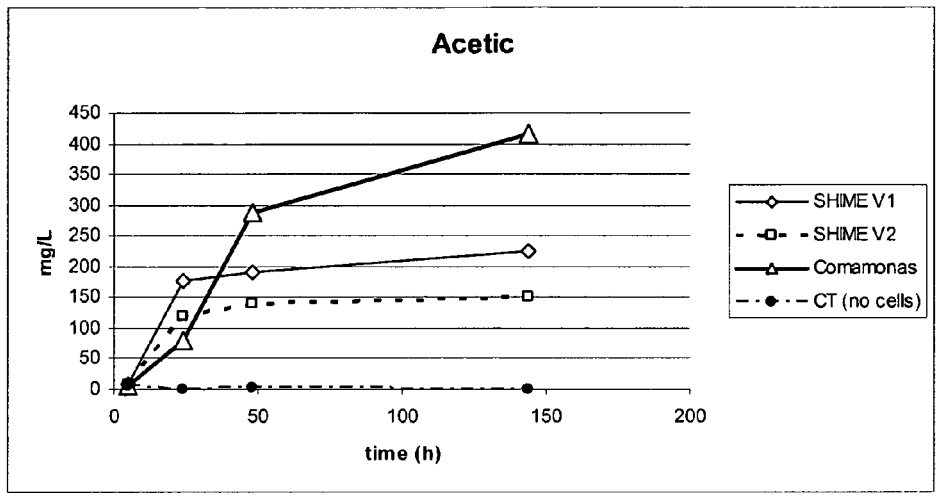
FIG. 1 is a graph showing that addition of commercial polyhydroxy-butyrate (PHB) to SHIME suspensions (vessel V1 and V2) gave rise to significant increased amounts of acetic acid.

In a preferred embodiment, the present invention provides the use of poly-3-hydroxybutyrate. Accordingly, particular embodiments of the invention relate to methods of modulating gut microflora and/or reducing or preventing bacterial infection in an animal comprising administering to the animal poly-3-hydroxybutyrate.

Poly-3-hydroxybutyrate is commercially available or can easily be prepared by a skilled person using processes and methods well-known in the art. For example, poly-hydroxybutyrate can be produced according to the disclosure of WO95/20615, WO95/33064, WO97/07229, WO97/07230 and WO97/15681. It is also known to produce PHAs by plant cells as it is disclosed in WO92/19747 and WO93/02187.

HB and/or PHB may be administrated to the animals as a component of a nutraceutical composition which is conventionally fed to animals. Thus, HB and/or PHB may be suitably administered to the animals as a component of the animal feed and/or in their drinking water.

Optionally the poly-3-hydroxybutyrate can be used alone or in combination with at least one depolymerase which supports the release of the active monomer in the gastro intestinal tract. If poly-3-hydroxybutyrate is used in a feed additive formulation it may be also used in combination with a GRAS (Generally Recognised As Safe) strain expressing such a depolymerase or a consortium of GRAS strains, expressing such a depolymerase.

The term GRAS strain as used herein denotes a "harmless strain" or "non-pathogenic and non-toxigenic strain" or a "microorganism with a GRAS status".

Alternatively, the poly-3-hydroxybutyrate (PHB) and the depolymerase are administered to the animal separately, either in a similar or in a different form (e.g. in separate feed formulations or in feed and/or drinking water formulations). Accordingly, a further aspect of the present invention provides such combinations and methods for using these combinations.

Examples of depolymerases which may be used according to the invention include (but are not limited to) extracellular PHB depolymerase enzymes, extracellular endo-type hydrolase enzymes, extracellular oligomer hydrolase enzymes and intracellular PHB depolymerase enzymes or a combination of the above mentioned enzymes.

PHB may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

In just a further aspect, the invention relates to the use in animal feed or drinking water of a strain of a microorganism, which produces PHB and to such strains, for modulation of the gut microflora. Accordingly, the present invention provides methods for modulating the gut microflora of an animal, which method comprises the step of administering to the animal an animal feed and/or drinking water comprising a microorganism which produces PHB. The microbial strain(s) producing PHB for use in the methods of the present invention is producing PHB extracellularly or intracellularly.

Optionally the said microbial strain can be used alone or in combination with at least one depolymerase which supports the controlled release of the active monomers in the gastro intestinal tract. According to this embodiment, the present invention provides methods for modulating the gut microflora of an animal, which method comprises the step of administering to the animal an animal feed and/or drinking water comprising a microorganism which produces PHB and a depolymerase or a strain of a microorganism which produces depolymerase.

The microbial strain(s) producing PHB and/or depolymerase for use in the methods of the present invention is cultivated in accordance with known methods, e.g. in a medium containing carbon and nitrogen sources, inorganic salts, etc., which can be assimilated by the host and under temperature, pH and aeration conditions suitable for efficient growing and expression of the desired product, PHB and/or depolymerase.

In particular embodiments, PHB is isolated from one or more bacterial strains for generation of a feed or drinking water component or as a feed additive for use in the methods of the invention. Isolation from the fermentation broth and/or the transformant and, if desired, purification of the PHB obtained including its compounding for human or animal usage can be effected in accordance with methods well-known in the art. For use in animal health and nutrition, however, no specific purification may be necessary. In this case PHB together with the biomass and/or other components of the fermentation broth may be further processed, for example by spray drying—to yield a commercially attractive product.

Examples of bacteria which are able to produce intracellular PHB in good quantities include strains from the genera of Proteobacteria as for example *Ralstonia* or *Rhodobacter*. In further particular embodiments, the strain is a strain of *Ralstonia eutropha* (ATCC 17699) or *Rhodobacter sphaeroides* (ATCC 35053).

Examples of bacteria which are able to produce extracellular PHB in good quantities include genetically engineered organisms, i.e. recombinant strains as for example a strain as disclosed in "Mutation in a tesB-like hydroxyacyl-coenzyme A-specific thioesterase gene causes hyperproduction of extracellular polyhydroxyalkanoates by Alcanivorax borkumensis SK2, Sabirova J S et al., JOURNAL OF BACTERIOLOGY 188 (24): 8452-8459, December 2006".

According to a particular embodiment, the PHB producing strain(s) used in the context of the present invention are further treated so as to enrich PHB production. Accordingly, the present invention provides enrichment cultures of PHB-producing strains for use in the methods of the invention. More particularly, the enriched strains of the present invention contain at least 10%, more particularly at least 15% PHB on total volatile suspended solids (VSS). Examples of methods of enrichment include cycles of freezing and thawing. In further embodiments, the biomass of one or more bacteria producing PHB is used in feed or drinking water or as a feed additive.

In the use according to the invention the PHB and/or the biomass can be fed to the animal before, after, or simultaneously with the diet. The latter is preferred.

It is a second object of the present invention to provide compositions, e.g. feed, drinking water and feed or drinking water additives comprising:
PHB and at least one depolymerase or a strain expressing such a depolymerase or
a strain which produces PHB and at least one depolymerase or a strain expressing such a depolymerase.

Further particular embodiments relate to combinations and kits of two or more compositions of feed, drinking water and feed or drinking water additives, wherein each of the compositions comprises one of (1) a PHB or strain producing PHB or (2) a depolymerase or a strain producing depolymerase. According to this embodiment the two or more compositions are packaged separately. The two or more compositions of the combinations and kits of the present invention can be combined prior to administration or are administered separately (sequentially or simultaneously) to the animal in the methods of the present invention.

Particular examples of compositions of the invention are the following:
An animal feed or drinking water additive comprising (a) PHB and a PHB depolymerase, (b) at least one fat-soluble vitamin, (c) at least one water-soluble vitamin, (d) at least one trace mineral, and/or (e) at least one macro mineral;
An animal feed or drinking water composition comprising (a) PHB and a PHB depolymerase and (b) a crude protein content of 50 to 800 g/kg feed;
An animal feed or drinking water additive comprising (a) a strain of microorganism as defined above and a PHB depolymerase, (b) at least one fat-soluble vitamin, (c) at least one water-soluble vitamin, (d) at least one trace mineral, and/or (e) at least one macro mineral;
An animal feed composition having a crude protein content of 50 to 800 g/kg and comprising a strain of or a consortium of microorganism(s) as defined above and a PHB depolymerase.

The PHB depolymerase is added to the compositions of the present invention as a pure enzyme, or in form of a biomass of a strain which is producing intracellular PHB depolymerase or as a probiotic strain which is producing extracellular PHB depolymerase. An example of such a probiotic strain is *Comamonas* testosterone (LMG19554).

The term "probiotic" generally refers to a non-pathogenic bacterium fed to animals, including birds, as a way to prevent colonization by pathogenic microorganisms. Probiotics may also be defined as live, or viable, micro-organisms which beneficially affect the intestinal balance of healthy and normally functioning humans and animals.

The so-called premixes are examples of animal feed additives of the invention. A premix designates a preferably uniform mixture of one or more micro-ingredients with diluent and/or carrier. Premixes are used to facilitate uniform dispersion of micro-ingredients in a larger mix.

In a particular embodiment, the PHB, in the form in which it is added to the feed, or when to being included in a feed additive, is well-defined. The term well-defined means that the PHB preparation is at least 20% pure. In other particular embodiments the well-defined PHB preparation is at least 30, 40, 50, 60, 70, or at least 80% pure.

A well-defined PHB preparation is advantageous. For instance, it is much easier to dose correctly to the feed a PHB that is essentially free from interfering or contaminating other compounds. The term dose correctly refers in particular to the objective of obtaining consistent and constant results, and the capability of optimizing dosage based upon the desired effect.

For the use in animal feed, however, the PHB need not be that pure; it may e.g. include other PHAs.

The PHB preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original PHB preparation, whether used according to (a) or (b) above.

PHB preparations with purities of this order of magnitude are in particular obtainable using recombinant methods of production, whereas they are not so easily obtained and also subject to a much higher batch-to-batch variation when the PHB is produced by traditional fermentation methods.

The PHB can be added to the feed in any form, be it as a relatively pure PHB, or in a mixture with other components intended for addition to animal feed, i.e. in the form of animal feed additives, such as the so-called pre-mixes for animal feed. For example the PHB or PHB containing biomass can be added to an animal diet in spray dried form as a dry pulver.

The amount of PHB administered to the animal is in the range from 0.05-5% based on the total weight of each feed fed to the animal, which corresponds to 500-50,000 ppm or mg/kg feed. In a preferred embodiment of the invention PHB being used in an amount sufficient to provide a daily dosage of 5 mg per kg body weight to about 500 mg per kg body weight of the subject to which it is to be administered.

In preferred embodiments the PHB is administered in one or more of the following amounts (dosage ranges): 0.01-500; 0.01-200; 0.01-100; 0.05-100; 0.1-10; 0.5-100; 0.5-50; 1-50; 1-10; 5-100; 10-100; all these ranges being in mg PHB per kg feed (ppm).

It is at present contemplated that the *Ralstonia* or the *Rhodobacter* strain is administered in form of dry biomass containing 100 to 500, for example 150 to 260 g PHB/kg biomass.

A probiotic strain which produces extracellular PHB depolymerase, as for example *Comamonas* testosterone (LMG19554), is preferably administered to the animal in the range from $10^6$-$10^8$ CFU/kg of feed.

The following are non-limiting particular examples of the gut microflora modulation effect obtained by PHB of the invention (changes as compared to a control without PHB of the invention):

(i) a decrease in the frequency with which *Salmonella* occurs in vivo, for example in piglets or in broilers, preferably determined after cultivation of ileo-rectal and/or caecal contents on (1) Selenite and Cystine and on (2) Rappaport Vassiliadis media, at 41.5° C., under slight agitation for 24 hours followed by transfer of 10 µl from both incubations to Hektoen, SMID and XLT4 media and incubation at 37° C. for 24 hours.
(ii) a decrease in the number of *Escherichia coli* in vivo, for example in piglets and/or broilers, preferably determined after cultivation of ileo-rectal and/or caecal contents, respectively, on *Coli*-ID chromogenic media, aerobically, at 37° C. for 24 hours;
(iii) a decrease in the number of other Enterobacteriaceae (other than *E. coli*) in vivo, for example in piglets, preferably determined after cultivation of ileo-rectal contents on a *Coli*-ID chromogenic media, aerobically, at 37° C. for 24 hours;
(iv) a decrease in the number of *Enterococcus* spp. in vivo, for example in piglets, preferably determined after cultivation of ileo-rectal contents on an Enterococci agar, aerobically, at 44° C. for 48 hours; and/or Still further, also in relation to the gut microflora modulating effect, and with reference to a control without PHB of the invention, PHB of the invention preferably:
(v) does substantially influence, e.g. reduce, the growth in vitro of harmful micro-organisms, such as bacteria, for example as isolated from piglet and/or broiler intestinal contents.

Maintenance of a balanced gut "microflora" aids a proper digestion and/or supporting immune system function and therefore which—in generally—results in an improved Feed Conversion Ratio (FCR).

According to the invention, the FCR may be determined on the basis of a broiler chicken growth trial comprising a first treatment in which PHB is added to the animal feed in a suitable concentration per kg feed, and a second treatment (control) with no addition of PHB or PHB containing biomass to the animal feed.

As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%.

A part from the PHB and/or the bacterial strain which produces PHB, the animal feed additives of the invention optionally contain at least one fat-soluble vitamin, and/or at least one water soluble vitamin, and/or at least one trace mineral, and/or at least one macro mineral.

Further, optional, feed-additive ingredients are coloring agents, e.g. carotenoids such as beta-carotene, astaxanthin, and lutein; aroma compounds; stabilisers; antimicrobial peptides; polyunsaturated fatty acids; reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with PHB or a bacterial strain of the invention, is an animal feed additive of the invention.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

Animal feed compositions or diets have a relatively high content of protein. Poultry and pig diets can be characterized as indicated in Table B of WO 01/58275, columns 2-3. Fish diets can be characterized as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least HB, preferably PHB, and/or at least one strain as described and/or claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source. It may also contain animal protein, such as Meat and Bone Meal, and/or Fish Meal, typically in an amount of 0-25%. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-30% rye; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. PHB(s) and/or the bacterial strain can be added as solid or liquid formulations.

In a third object the present invention relates to the use of hydroxybutyrate and/or poly-hydroxybutyrate, preferably 3-hydroxybutyrate and/or poly-3-hydroxybutyrate as antimicrobial agents, in particular as anti-bacterial, anti-fungal and/or malodour counteracting agent. Accordingly, the present invention provides methods for reducing or preventing bacterial and/or fungal infection and/or malodour in an animal, the method comprising, administering to the animal of hydroxybutyrate and/or poly-hydroxybutyrate, preferably 3-hydroxybutyrate and/or poly-3-hydroxybutyrate, more particularly as a feed or drinking water component. Particular embodiments of the invention relate to the use of poly-hydroxybutyrate as the sole antimicrobial agent in animal feed or drinking water.

Furthermore the invention relates to antimicrobial compositions comprising hydroxybutyrate and/or poly-hydroxybutyrate, preferably 3-hydroxybutyrate and/or poly-3-hydroxybutyrate, their use in feed and in pharmaceutical applications, including veterinary applications, e.g. for the manufacture of medicaments. The invention also relates to the use of microbial strains producing hydroxybutyrate and/or poly-hydroxybutyrate, preferably 3-hydroxybutyrate and/or poly-3-hydroxybutyrate as antimicrobial agents. Specific embodiments relate to enrichment strains of PHB-producing bacteria for use as antimicrobial agents.

Medicaments are pharmaceutical formulations used to treat a disease. A disease can be defined as an impairment of health or a condition of abnormal functioning; in other words: A condition of being sick from a particular cause.

The term "antimicrobial agent" is defined herein as a chemical compound or composition which has antimicrobial activity when applied to the animal body, i.e. which either itself shows antimicrobial activity or which—as a "prodrug"—generates antimicrobial activity after chemical modification, in case of PHB, after depolymerisation.

The term "antimicrobial activity" (or "antimicrobial effect") means a capability of killing and/or inhibiting or preventing growth of microbial cells. Examples of microbial cells are cells of microorganisms.

The term "microorganisms" include bacteria, protozoa, algae, fungi (including yeast), and viri.

Antimicrobial activity may, e.g., be bactericidal, bacteriostatic, fungicidal, fungistatic, and/or virucidal. The term "bactericidal" is to be understood as capable of killing bacterial cells; the term "bacteriostatic" as capable of inhibiting bacterial growth, i.e. inhibiting growing bacterial cells; the term "fungicidal" as capable of killing fungal cells; the term "fungistatic" as capable of inhibiting fungal growth, i.e. inhibiting growing fungal cells; and the term "virucidal" is to be understood as capable of inactivating virus.

In the context of the present invention the term "inhibiting growth of microbial cells" is intended to mean that the cells are in the non-growing state, i.e., that they are not able to propagate.

In particular embodiments of the invention PHB gives rise to SCFAs, which are (i) capable of inhibiting bacterial growth, viz. bacteriostatic; and/or (ii) capable of killing bacterial cells, viz. bactericidal.

For purposes of the present invention antimicrobial activity may be determined by the Minimum Inhibitory Concentration (MIC) assay, which is described by the NCCLS (National Committee for Clinical Laboratory Standards, in: Methods for Determining Bactericidal Activity of Antimicrobial Agents; Approved Guideline. National Committee for Clinical Laboratory Standards (M26-A), Vol 19, 1999).

Briefly, the MIC is determined by inoculating serial two fold dilutions of PHB in Mueller-Hinton Broth (MHB) with a culture of the actively growing microorganism and incubating at 35° C. MICs are determined after 24 hours of incubation and defined as the lowest concentration of PHB with no visible growth.

For the present purposes antimicrobial activity against a certain microorganism species is acknowledged for compounds having a MIC value below 300 microgram/ml.

Microbes of potential interest include, but are not limited to, Gram-positive bacteria as for example *Clostridium*, or to Gram-negative bacteria, for example: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi*, *S. typhimurium*; *Serratia* sp.; *Shigella* sp.; *Pseudomonas* sp., e.g. *P. aeruginosa*; *Yersinia* sp., e.g. *Y. pestis*, *Y. pseudotuberculosis*, *Y. enterocolitica*; *Franciscella* sp.; *Pasturella* sp.; *Vibrio* sp., e.g. *V. cholerae*, *V. parahaemolyticus*; *Campylobacter* sp., e.g. *C. jejuni*; *Haemophilus* sp., e.g. *H. influenzae*, *H. ducreyi*; *Bordetella* sp., e.g. *B. pertussis*, *B. bronchiseptica*, *B. parapertussis*; *Brucella* sp.,

*Neisseria* sp., e.g. *N. gonorrhoeae*, *N. meningitidis*, etc. Other bacteria of interest include *Legionella* sp., e.g. *L. pneumophila*; *Listeria* sp., e.g. *L. monocytogenes*; *Mycoplasma* sp., e.g. *M. hominis*, *M. pneumoniae*; *Mycobacterium* sp., e.g. *M. tuberculosis*, *M. leprae*; *Treponema* sp., e.g. *T. pallidum*; *Borrelia* sp., e.g. *B. burgdorferi*; *Leptospirae* sp.; *Rickettsia* sp., e.g. *R. rickettsii*, *R. typhi*; *Chlamydia* sp., e.g. *C. trachomatis*, *C. pneumoniae*, *C. psittaci*; *Helicobacter* sp., e.g. *H. pylori*, etc.

Non-bacterial pathogens of potential interest include fungal and protozoan pathogens, e.g. *Plasmodia* sp., e.g. *P. falciparum*, *Trypanosoma* sp., e.g. *T. brucei*; shistosomes; *Entaemoeba* sp., *Cryptococcus* sp., *Candida* sp., e.g. *C. albicans*; etc.

In particular embodiments PHB or PHB containing biomass of the invention—when applied to the animal—has antimicrobial activity against at least one of the following specific microorganism species and strains: *Salmonella* spp, *Escherichia coli*, *Bacillus cereus*, *Corynebacterium jeikeium*, *Enterococcus faecalis*, *Enterococcus faecium*, *Micrococcus luteus*, *Staphylococcus aureus*, *Staphylococcus epidermidis*, *Streptococcus pneumoniae*, *Vibrio campbellii*, *Listeria monocytogenes* and *Listeria ivanovii*.

In a specific particular embodiment, the invention is related to the use of PHB or PHB containing biomass as antimicrobial agent in order to prevent animals, preferably water animal, more preferably shrimp, from infections caused by pathogenic *Vibrio campbellii*.

In another specific particular embodiment, the invention is related to the use of PHB or PHB containing biomass as antimicrobial agent in order to prevent monogastric animals, for example broiler chickens from infections caused by pathogenic *Clostridium* sp and *Salmonella* spp and for example piglets form infections caused by pathogenic *Escherichia coli*.

Accordingly, the present invention provides methods for preventing and/or reducing infection of animals, more particularly water animals and monogastric animals, which methods comprise, administering to the animal PHB or PHB-containing biomass, more particularly as a component of the animal feed or drinking water.

As defined in the introduction part the term "nutraceutical" as used herein denotes a usefulness in both the nutritional and pharmaceutical field of application. Thus, PHB or HB may be used as antimicrobial agent in animal feed or in pharmaceutical formulation.

Generally, the pharmaceutical formulation of the invention comprises an effective amount of the antimicrobial HB and/or PHB of the, which is sufficient to inhibit growth of the microorganism in question and therefore to improve the general health status of animals.

HB and/or PHB, may be used (i) in therapy, i.e. for treatment of a disease, and/or (ii) for prophylaxis, i.e. treatment to prevent the onset of a particular disease ("primary" prophylaxis), and/or the recurrence of symptoms in an existing infection that has been brought under control ("secondary" prophylaxis, maintenance therapy).

PHB may be used (a) in veterinary medicine, which is the application of medical, diagnostic, and therapeutic principles to companion, domestic, exotic, wildlife, and production animals; and/or (b) in human medicine.

Therefore, the invention also relates to medicaments including veterinary compositions comprising PHB of the invention.

The invention furthermore relates to the use of PHB in the preparation of a medicament for the treatment of a microbial infection; and to a method of medical treatment comprising administering PHB to an individual, such as a human being or an animal, in need of medical treatment.

The invention in particular relates to the treatment of a disease caused by microorganisms, e.g. by microbial infections. The treatment with PHB of the invention may serve to control or combat microorganisms as defined above, such as fungi or bacteria, e.g. Gram positive or Gram negative bacteria. In a particular embodiment of the invention, the microbial infections envisaged are infections which also or only affect the upper gut, more particularly the small intestine.

The compounds of this invention can be incorporated into a variety of pharmaceutical formulations for therapeutic administration. More particularly, the compounds of the present invention can be formulated into pharmaceutical compositions by combination with appropriate, pharmaceutically acceptable carriers or diluents. Pharmaceutical compositions may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration.

The composition may further comprise another pharmaceutically active agent, such as an additional biocidal agent, such as antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monolactams; aminoglycosides; tetracyclines; macrolides; lincomycins; polymyxins; sulfonamides; quinolones; chloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

Pharmaceutical formulations of the invention may be administered to a host suffering from or predisposed to a microbial infection. Administration may be topical, localized or systemic, depending on the specific microorganism, preferably it will be localized. Generally the dose of the antimicrobial PHB of the invention will be sufficient to decrease the microbial population by at least about 50%, usually by at least 1 log, and may be by 2 or more logs of killing. The PHB (or compounds) of the present invention may be administered at a dosage that reduces the microbial population while minimizing any side-effects. It is contemplated that the composition will be obtained and used under the guidance of a physician or veterinarian for in vivo use.

Various methods for administration may be employed. PHB formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously.

The invention described and claimed herein is not to be limited in scope by the specific embodiments hereinafter disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

EXAMPLES

Example 1

Animal Feed Additive

An animal feed additive is prepared by adding 0.5 g of crystalline PHB (Commercial PHB from Goodfellow, Huntingdon, UK, final conc. 2.5 g/L) to the following premix (per kilo of premix):

| 1100000 | IE | Vitamin A |
|---|---|---|
| 300000 | IE | Vitamin D3 |
| 4000 | IE | Vitamin E |
| 250 | mg | Vitamin B1 |
| 800 | mg | Vitamin B2 |
| 1200 | mg | Ca-D-Panthothenate |
| 500 | mg | Vitamin B6 |
| 2.5 | mg | Vitamin B12 |
| 5000 | mg | Niacin |
| 10000 | mg | Vitamin C |
| 300 | mg | Vitamin K3 |
| 15 | mg | Biotin |
| 150 | mg | Folic acid |
| 50004 | mg | Cholin chloride |
| 6000 | mg | Fe |
| 3000 | mg | Cu |
| 5400 | mg | Zn |
| 8000 | mg | Mn |
| 124 | mg | I |
| 60 | mg | Co |
| 29.7 | mg | Se |
| 9000 | mg | Lasalocid Sodium (Avatec) |
| 17.3% | | Ca |
| 0.8% | | Mg |
| 11.7% | | Na |

Example 2

Animal Feed

A broiler grower diet having the following composition (%, w/w) is prepared by mixing the ingredients. Wheat, rye and SBM 48 are available from Moulin Moderne Hirsinque, Hirsingue, France. After mixing, the feed is pelleted at a desired temperature, e.g. about 70° C. (3×25 mm).

| Wheat | 46.00 |
|---|---|
| Rye | 15.00 |
| Soy Bean Meal (SBM 48) | 30.73 |
| Soybean oil | 4.90 |
| DL-Methionine | 0.04 |
| DCP (Di-Calcium Phosphate) | 1.65 |
| Limestone | 0.43 |

-continued

| Salt | 0.15 |
|---|---|
| TiO2 | 0.10 |
| Animal feed additive (above) | 1.00 |

The resulting animal feed comprises 500 mg PHB per kg (500 ppm).

Additional animal feed and feed additive compositions are prepared in the same manner, however substituting 500 mg PHB with a biomass of a strain of *Ralstonia eutropha* (ATCC 17699) or *Rhodobacter sphaeroides* (ATCC 35053) containing approximately 250 g PHB/kg biomass.

Example 3

Piglet Feed Containing Crystalline PHB and a Depolymerase

A piglet feed containing 0.5 g of crystalline PHB (Commercial PHB from Goodfellow, Huntingdon, UK, final conc. 2.5 g/L can be prepared by mixing the following ingredients together using a conventional mixing apparatus at room temperature.

| Ingredient | Amount (kg) |
|---|---|
| Wheat | 32.6 |
| Maize | 18.7 |
| Rice | 5.0 |
| Wheat bran | 9.0 |
| Soybean meal | 23.0 |
| Soy oil | 2.0 |
| Wheat starch | 4.5 |
| Minerals* | 2.9 |
| Synthetic amino acids premix** | 0.8 |
| Vitamins and trace elements premix*** | 1.0 |
| poly-3-hydroxybutyrate premix (10% in wheat starch) | 0.5 |
| Probiotic Comamonas tesoteronie (LMG19554)**** | $10^6$-$10^8$ CFU |

*Sea salt, dicalcium phosphate and calcium carbonate;
**Lysine, methionine and threonine;
***Vitamins A, E, D3, K3, B1, B2, B6, B12, C, biotine, folic acid, niacin, pantothenic acid, choline chloride, copper sulphate, iron sulphate, manganese oxide, zinc oxide, cobalt carbonate, calcium iodide and sodium selenite.
****Comamonas tesoteronie ($10^8$ Colony forming Units (CFU) in the form of strain Comamonas tesoteronie (LMG19554))

Example 4

Pig Feed Containing PHB and a Depolymerase Produced by Microbial Strains

A growing pig feed containing poly-3-hydroxybutyrate can be prepared by mixing the following ingredients together using a conventional mixing apparatus at room temperature.

| Ingredient | Amount (kg) |
|---|---|
| Soybean meal | 18.0 |
| Maize | 52.3 |
| Barley | 14.0 |
| Oat meal | 6.0 |
| Wheat bran | 5.2 |
| Soy oil | 2.0 |
| Minerals* | 1.5 |
| Synthetic amino acids premix** | 0.5 |

-continued

| Ingredient | Amount (kg) |
|---|---|
| Vitamins and trace elements premix*** | 1.0 |
| Biomass of Rhodobacter sphaeroides (ATCC 35053)***** | 0.5 |
| Probiotic Comamonas testosteroni (LMG19554)**** | $10^6$-$10^8$ CFU |

*****Biomass of Rhodobacter sphaeroides prepared as described in Example 5.

Example 5

Effect of Polyhydroxy-Butyrate (PHB) on the Growth Performance of Broiler Chickens Over Two Weeks

Experimental Approach

Preparation of PHB Containing Biomass from *Rhodobacter sphaeroides* (ATCC 35053)

*Rhodobacter sphaeroides* ATCC 35053 was obtained from the American Type Culture Collection (Manassas (Va.), USA) and is classified as safety level 1.

The culture was initiated from frozen cell suspensions (stored as 10-25% glycerol stocks at −80° C.). The inoculum for the fed-batch fermentations were prepared in multiple 2-liter baffled shake flasks containing 400 ml of inoculum medium containing (per liter distilled water): D-glucose.$H_2O$, 33 g; yeast extract, 20 g; NaCl, 0.5 g; $MgSO_4$.$7H_2O$, 0.5 g and trace amounts of Fe, Zn, Mn and Ni salts. Two milliliters of thawed cell suspension were used as inoculum for each flask. The precultures were incubated at 30° C. with shaking at 250 rpm for 28 hours. Main cultures were grown as standard fed-batch process in a 500 L bioreactor (B. Braun Biotech International, Melsungen, Germany) containing medium 2 having the following composition (per liter distilled water): D-glucose.$H_2O$, 16 g; yeast extract, 13 g; NaCl, 0.9 g; $MgSO_4$.$7H_2O$, 0.9 g; $(NH_4)_2Fe(SO_4)_2$.$6H_2O$, 0.72 g; $CaCl_2$.$2H_2O$, 0.675 g; $FeCl_3$.$6H_2O$, 0.09 g; $(NH_4)_2SO_4$, 1.44 g, $ZnSO_4$.$7H_2O$, 0.054 g; $MnSO_4$.$H_2O$, 0.018 g; $NiSO_4$.$6H_2O$, 0.002 g; antifoam, 0.1 ml; $KP_2$ solution, 4.5 ml. The composition of $KP_2$ solution is (per liter distilled water): $K_2HPO_4$, 200 g; $NaH_2PO_4$.$2H_2O$, 200 g. The feeding solution used in all processes had the following composition (per liter distilled water): D-glucose.$H_2O$, 770 g. The initial volume in the bioreactor (after inoculation) was about 200 L.

Inoculation: Shake flask cultures were pulled together in order to achieve an initial inoculum volume of 5% in the bioreactor.

Process conditions: Fermentation conditions were automatically controlled as follows: 30° C., pH 7.1 (pH controlled with addition gaseous $NH_4OH$), dissolved oxygen controlled at a minimum of 10% relative value (in cascade with agitation), minimum agitation of 300 rpm and an aeration rate of 0.5 v.v.m. (relative to initial volume). The cultivations proceeded under these conditions without addition of feed solution (batch phase). After some time, a decrease in agitation speed, cessation of base consumption, a sharp pH increase and a decrease in $CO_2$ production were the indication that the initial glucose was exhausted and the feeding was started.

Feed profile: A standard feed profile was defined as follows (from feeding start point): ramp from 2.5 kg/h to 3.8 kg/h in 10 hours, continue at 3.8 kg/h for rest of the fermentation. The fermentation process was ended when the maximum working volume of about 400 L was reached.

Cell inactivation and drying: The resulting fermentation broth was pasteurized at 85° C. for 1 hour resulting in complete inactivation of the microorganism. The inactivated broth was then spray dried resulting in an ease flowing powder with about 5% moisture content.

The resulting *R. sphaeroides* dry biomass obtained with the procedure described above was analyzed for PHB content. The concentration of PHB in biomass was 253 g PHB/kg dry biomass.

Experimental Plan A

Growth trial: day 8 to day 22 (pre-experimental period from day 1 to day 8)
Diets: wheat/rye/SBM48 diet (see feed composition)
Feeding: pellets ad libitum
Treatments: Control
    Avilamycin
    Biomass *Rhodobacter sphaeroides* (PHB) 1 g/kg
    Biomass *Rhodobacter sphaeroides* (PHB) 5 g/kg
    After mixing the feed was pelleted at about 70° C. (3×25 mm).
Replicates: 6 groups of 6 male chickens (ROSS PM3) per treatment
Housing: wire-floored battery cages in an environmentally controlled room
Products: Avilamycin, Maxus G 200, lot 836CR3,
    *Rhodobacter Sphaeroides* biomass, 253 g PHB/kg, dry powder, prepared as described above A growth performance trial with broiler chickens was performed from day 8 to day 22. The chickens were housed in wire-floored battery cages. From day-old until day 8, the chickens were fed a pre-experimental diet based on wheat, maize and soybean meal. In the experimental period (day 8 to 22) the chickens received diets based on wheat, rye and soybean meal (composition see Table 1). Groups of birds were weighed on days 8, 15, and 22. The feed consumption for the intermediate periods was determined and body weight gain and feed conversion ratio were calculated.

Beside an un-supplemented control treatment and a positive control containing 10 mg of the antibiotic Avilamycin per kg feed, *Rhodobacter Sphaeroides* biomass was included at dosages of 1 and 5 g per kg feed, corresponding to 0.253 and 1.265 g of PHB per kg feed, respectively.

TABLE 1

Feed composition of the experimental diet

| Ingredients (%): | Pre-experimental period | Growth trial |
|---|---|---|
| Maize | 37.10 | — |
| Wheat | 20.00 | 27.30 |
| Rye | — | 30.00 |
| SBM 48 | 36.20 | 34.20 |
| Soybean oil | 2.80 | 4.50 |
| DL-Methionine | 0.20 | 0.20 |
| DCP | 1.80 | 2.00 |
| Limestone | 0.80 | 0.70 |
| Salt | 0.10 | 0.10 |
| Premix[1] | 1.00 | 1.00 |

[1]Including Avatec

Results

At a dose of 1 g per kg, the *Rhodobacter Sphaeroides* biomass protein improved the weight gain of the chickens slightly compared to the negative control (Table 2). At a dose of 5 g per kg, the *Rhodobacter Sphaeroides* biomass improved the weight gain and the feed conversion ratio of the chickens compared to the negative control. The positive effects of the highest inclusion of *Rhodobacter Sphaeroides* biomass were in the same range as those of the positive control supplemented with the antibiotic Avilamycin.

The results of the present trial demonstrated that the *Rhodobacter Sphaeroides* biomass containing about 25% PHB improved the performance of broiler chickens over two weeks.

TABLE 2

Performance of broiler chickens over the growth cycle
(day 8 to day 22); mean ± stdev

| | Control | Avilamycin | Biomass Rhodobacter sphaeroides | |
|---|---|---|---|---|
| | | | Dose | |
| | — | 10 mg/kg | 1.0 g/kg | 5.0 g/kg |
| | | cages × birds | | |
| | 6 × 6 | 6 × 6 | 6 × 6 | 6 × 6 |
| | | Day 8-15 | | |
| Weight gain (g/bird) | 315 ± 22 | 334 ± 20 | 326 ± 17 | 339 ± 19 |
| Feed intake (g/bird) | 553 ± 79 | 552 ± 43 | 578 ± 30 | 551 ± 36 |
| Feed conversion (g feed/g gain) | 1.750 ± 0.155 | 1.652 ± 0.090 | 1.776 ± 0.115 | 1.629 ± 0.105 |
| | | Day 15-22 | | |
| Weight gain (g/bird) | 444 ± 52 | 476 ± 24 | 464 ± 35 | 462 ± 60 |
| Feed intake (g/bird) | 869 ± 109 | 889 ± 67 | 909 ± 69 | 875 ± 96 |
| Feed conversion (g feed/g gain) | 1.956 ± 0.117 | 1.867 ± 0.078 | 1.967 ± 0.154 | 1.904 ± 0.160 |
| | | Day 8-22 | | |
| Weight gain (g/bird) | 760 ± 70 | 810 ± 39 | 789 ± 36 | 801 ± 78 |
| | 100.0 | 106.7 | 103.9 | 105.5 |
| Feed intake (g/bird) | 1426 ± 181 | 1441 ± 100 | 1487 ± 89 | 1427 ± 129 |
| | 100.0 | 101.1 | 104.3 | 100.1 |
| Feed conversion (g feed/g gain) | 1.874 ± 0.117 | 1.778 ± 0.072 | 1.886 ± 0.132 | 1.786 ± 0.129 |
| | 100.0 | 94.9 | 100.7 | 95.3 |

Compared to a second trail with crystalline PHB (Polyhydroxybutyrate 98%/Polyhydroxy-valerate 2%—Biopolymer Powder from Goodfellow), a higher dosage of the crystalline material was needed to obtain comparable improvements as it is illustrated in Table 3.

TABLE 3

Performance of broiler chickens over the growth cycle (day 8 to day 29);
mean ± stdev

| | Control | Avilamycin | Polyhydroxybutyrate (PHB) | | | |
|---|---|---|---|---|---|---|
| | | | Dose | | | |
| | — | 10 mg/kg | 0.5 g/kg | 1.0 g/kg | 2.0 g/kg | 4.0 g/kg |
| | | | cages × birds | | | |
| | 6 × 6 | 6 × 6 | 12 × 6 | 12 × 6 | 12 × 6 | 12 × 6 |
| | | | Day 8-29 | | | |
| Weight gain (g/bird) | 1283 ± 84 | 1367 ± 85 | 1273 ± 99 | 1292 ± 56 | 1306 ± 97 | 1322 ± 92 |
| % | 100.0 | 106.6 | 99.2 | 100.7 | 101.8 | 103.1 |
| Feed intake (g/bird) | 2379 ± 155 | 2402 ± 196 | 2370 ± 153 | 2494 ± 159 | 2453 ± 235 | 2412 ± 220 |
| % | 100.0 | 101.0 | 99.6 | 104.8 | 103.1 | 101.4 |
| FCR (g feed/g gain) | 1.858 ± 0.099 | 1.756 ± 0.079 | 1.867 ± 0.110 | 1.931 ± 0.111 | 1.881 ± 0.156 | 1.823 ± 0.086 |
| % | 100.0 | 94.5 | 100.5 | 104.0 | 101.3 | 98.2 |

Example 6

Effect of Crystalline PHB (as Only Carbon Source) on the Volatile Fatty Acid Profile of a Mixed Gut Microbial Community Experimental Approach Commercial PHB (Goodfellow, Huntingdon, UK, final conc. 2.5 g/L) was subjected to 1 h of simulated stomach digestion and 4 h of simulated duoden digestion in penicillin vials.

Samples from two vessels of the SHIME were centrifuged and washed with physiological solution (containing thioglycolate 1 g/L, to assure anoxic conditions) to eliminate any carbon source. (Detailed characteristics of the so called SHIME reactor can be found in "De Boever, P., Deplancke, B., and Verstraete, W., 2000, Fermentation by gut microbiota cultured in a simulator of the human intestinal microbial ecosystem is improved by supplementing a soygerm powder. *J Nutr* 130: 2599-2606").

Cell pellets were resuspended in 40 mL of physiological solution (No thyoglycolate) and added to the digested PHB suspensions. Negative control consisted in 40 mL of physiological solution without cells added. The washing step and dilution in physiological solution were done to simulate a culture under "starvation" conditions, where no other C-source was present, with concomitant induction of PHB depolymerase.

Vials were flushed with N2 and incubated at 37° C.

Results

I. Organic Acids (Quantified by HPLC)

From the results shown in FIG. 1, it can be observed that addition of commercial PHB, pre-treated to simulate stomach and duoden digestion, to SHIME suspension (vessel V1 and V2) gave rise to significantly increased amounts of acetic acid.

As a positive control treatment, a washed cell culture of *Comamonas testosteroni* with PHB-depolymerase activity was incubated with (pre-digested) PHB. The negative control treatment consisted of sterile treatment of pre-digested PHB (without biomass).

It is hypothesized that (pre-digested) PHB is first converted to hydroxybutyric/butyric acid, by PHB-depolymerase action, which is then instantly converted to acetate. Indeed, acetate was found to accumulate during the experiment.

2. VFAs (Quantified by GC-FID)

The production of volatile fatty acids (VFA) from pre-digested PHB in both SHIME suspensions (V1 and V2) and in a pure culture of *Comamonas testosteroni*, was additionally quantified by GC-FID.

Figure 2:
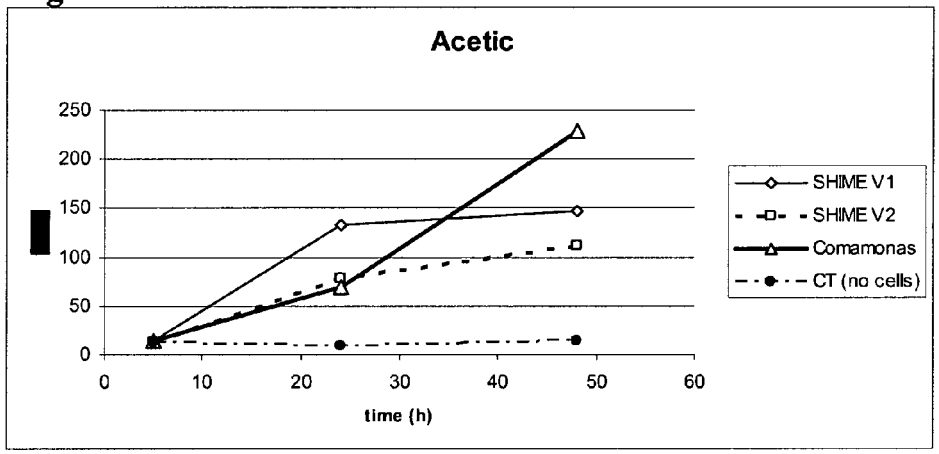
FIGS. 2A, 2B, and 2C are graphs showing acetic, butyric, and propionic acid production, respectively.
Figure 2:
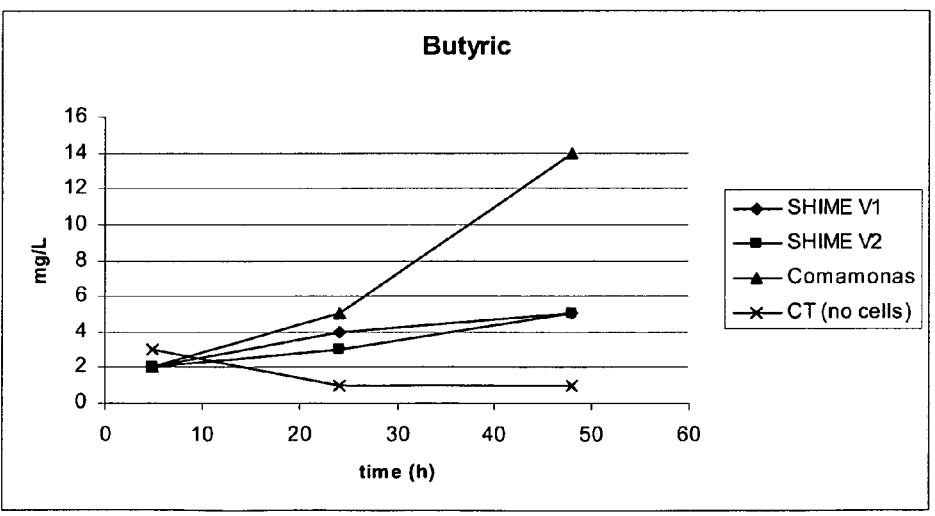
Figure 2:
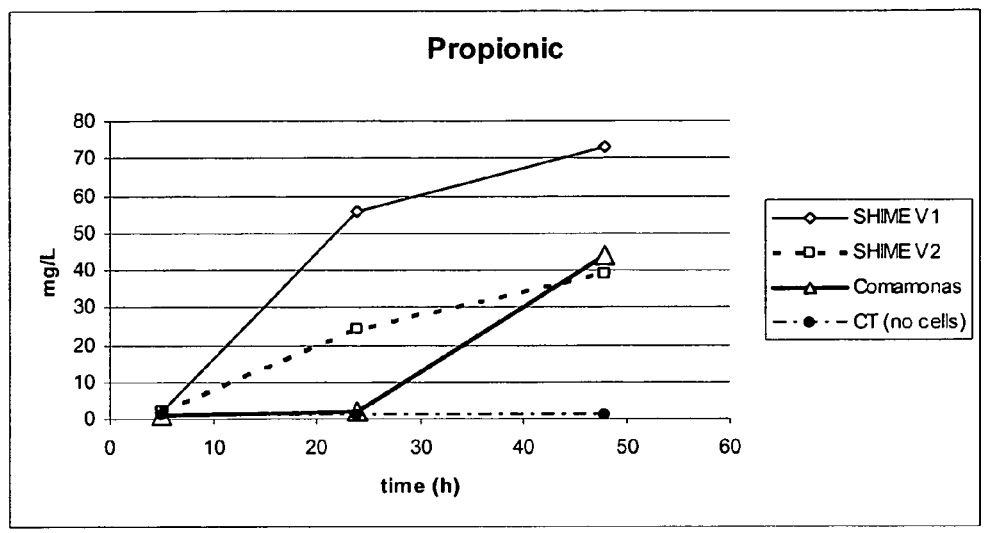

From FIGS. 2a, b and c it can be observed that the trend in acetic acid (incl. butyric and propionic) production is similar to what was observed by HPLC: Highest production in the *Comamonas* culture, somewhat lower production by the two PHB samples with a plateau value being reached after 24 hours, and no significant VFA production in the sterile negative controls (CT).

Example 7

3-Hydroxybutyrate and Hydrolyzed poly-3-hydroxybutyrate-Accumulating Bacteria Inhibit Growth of Enteric Pathogens and Increase Butyric and Acetate Levels in the In Vitro Human Gut Experimental Approach Microorganisms and Culture Media

*Ralstonia eutropha* (ATCC 17699) used as PHB-accumulating bacteria were enriched in a sequencing batch reactor inoculated with activated sludge on a laboratory scale polyphosphate-accumulating reactor as described by Serafim et al. Optimization of polyhydroxybutyrate production by mixed cultures submitted to aerobic dynamic feeding conditions, Biotechnol. Bioeng. 87, 145-160, 2004.

All incubations were performed in penicillin vials using fecal suspensions taken from the ascending vessel of the SHIME reactor running under normal feeding conditions. The feed matrix consisted of a carbohydrate-based medium containing arabinogalactan (1 g/L), pectin (2 g/L), xylan (1 g/L), starch (4.2 g/L), glucose (0.4 g/L), yeast extract (3 g/L), peptone (1 g/L), mucin (4 g/L), cysteine (0.5 g/L), $KH_2PO_4$ (5.3 g/L) and $Na_2HPO_4$ (1.4 g/L). Samples were sealed and flushed with $N_2$ during 30 min to assure anaerobic conditions and incubated under agitation at 37° C. All assays were performed in duplicate.

Microbial Counts

Decimal dilutions of the samples were plated and incubated at 37° C. Counts of *Salmonella* and coliforms were performed on *Salmonella*-agar (Chromagar, Paris, France) and McConkey-agar (Oxoid, Basingstoke, UK), respectively. Additional counts were performed on MRS-agar (Oxoid) (lactobacilli), *Enterococcus*-agar (Difco, Sparks, Md., USA) (enterococci) or TSC-agar (Merck, Darmstadt, Germany) (clostridia).

Determination of SCFAs

SCFAs were extracted with diethyl ether and determined with a Di200 gas chromatograph (Shimadzu's-Hertogenbosch, The Netherlands). The GC was equipped with a capillary free fatty acid column [EC-1000 Econo-Cap column (Alltech, Laarne, Belgium), 25 m×0.53 mm; film thickness 1.2 μm] a flame ionization detector and a Delsi Nermag 31 integrator (Thermo Separation Products, Wilrijk, Belgium). Nitrogen was used as carrier gas at a flow rate of 20 mL/min. The column temperature and the temperature of the injector and detector were set at 130° C. and 195° C. respectively. Quantification of PHB and crotonic acid was performed by HPLC using an Aminex HPX-87H ion-exchange organic acids column (300×7.8 mm) with 0.014 $NH_2SO_4$ at a flow rate of 0.7 ml/min as solvent. The elution peaks were monitored at 210 nm with a Dionex UV detector (Tienen, Belgium).

Stomach and Small Intestine Digestion

Commercial PHB (Goodfellow, Huntingdon, UK), PHB-cells or feed matrix were suspended in penicillin vials containing 20 mL of a solution of $KHCO_3$ (0.1 M) and NaCl (0.1 M) adjusted to pH 1.5 with HCl. Afterwards, 0.625 mL of pepsine solution (320 mg/L) were added and the suspension was incubated 2 h at 37° C. After stomach digestion, 20 mL of pancreatic juice containing $NaHCO_3$ (12.5 g/L), oxgall (6 g/L) and pancreatine (0.9 g/L) were added. The pH of the suspension was adjusted to 6.3 and samples were incubated under agitation for 6 h at 37° C.

Effect of PHB on Colon Microbiota

Samples from the ascending colon compartment of the SHIME reactor were supplemented with 10 g/L of 3-hydroxybutyrate (PHB) (Sigma-Aldrich, Bornem, Belgium) and incubated at 37° C. Microbial counts and SCFAs levels were determined as described above.

Effect of PHB and PHB as Only Carbon Sources

SHIME suspensions were centrifuged for 10 min at 7000× g, washed twice with physiological solution containing 1 g/L of thioglycolate, resuspended in mineral medium containing 1 g/L of 3 HB or 2.5 g/L of commercial PHB and incubated at 37° C. The mineral salts medium contained (per liter of distilled water) 600 mg $MgSO_4.7H_2O$, 160 mg $NH_4Cl$, 100 mg EDTA, 92 mg $K_2HPO_4$, 45 mg $KH_2PO_4$, 70 mg $CaCl_2.2H_2O$ and 2 ml/L of trace solution. The trace solution consisted of (per liter of distilled water) 1500 mg $FeCl_3.6H_2O$, 150 mg $H_3BO_3$, 150 mg $CoCl_2.6H_2O$, 120 mg $MnCl_2.4H_2O$, 120 mg $ZnSO_4.7H_2O$, 60 mg $Na_2MoO_4.2H_2O$, 30 mg $CuSO_4.5H_2O$. Basal acetate or butyrate production by intestinal bacteria was discarded by incubation of a control without PHB or PHB.

Effect of Untreated PHB-Cells on the Colon Microbiota 1.3 g of a lyophilized methylotrophic PHB-containing culture (PHB-cells) was subjected to stomach and small intestine digestion. 40 ml of SHIME suspension were added and samples incubated at 37° C. The same amount of a dried culture of not-PHB containing bacteria (*Brachymonas denitrificans*) was added in control samples to balance the effect of cell biomass as a substrate for intestinal bacteria.

Hydrolysis of PHB-Cells

PHB-cells were digested with 0.5 M NaOH or HCl at different times and temperatures. Quantification of degradation products was determined by HPLC as described above and the degree of hydrolysis was calculated with respect to the initial amount of PHB.

Effect of Hydrolyzed PHB-Cells on Ileum Microbiota

PHB-cells were digested with NaOH 0.5 M at 100° C. for 4 h and the resultant suspension neutralized with HCl. Different feeding solutions were prepared substituting part of the original nutrients (100%, 50%, 20%, 10% or 0% in dry matter) by digested PHB-cells, being the final amount of solids equivalent for all feed solutions. Samples were subjected to stomach and small intestine digestion as described above. Afterwards ⅒ of total volume of sample taken from the colon ascending vessel of the SHIME reactor was added to mimic the microbial environment of the ileum. In order to discard any inhibitory effect of NaCl present due to the NaOH treatment and neutralization with HCl, an additional control containing not-supplemented feeding was added with 2.6% of NaCl, equivalent to the amount present in the sample containing 100% PHB-cells. No effect of NaCl addition was observed.

Results

Effect of PHB on the Colon Microbiota

Figure 3:
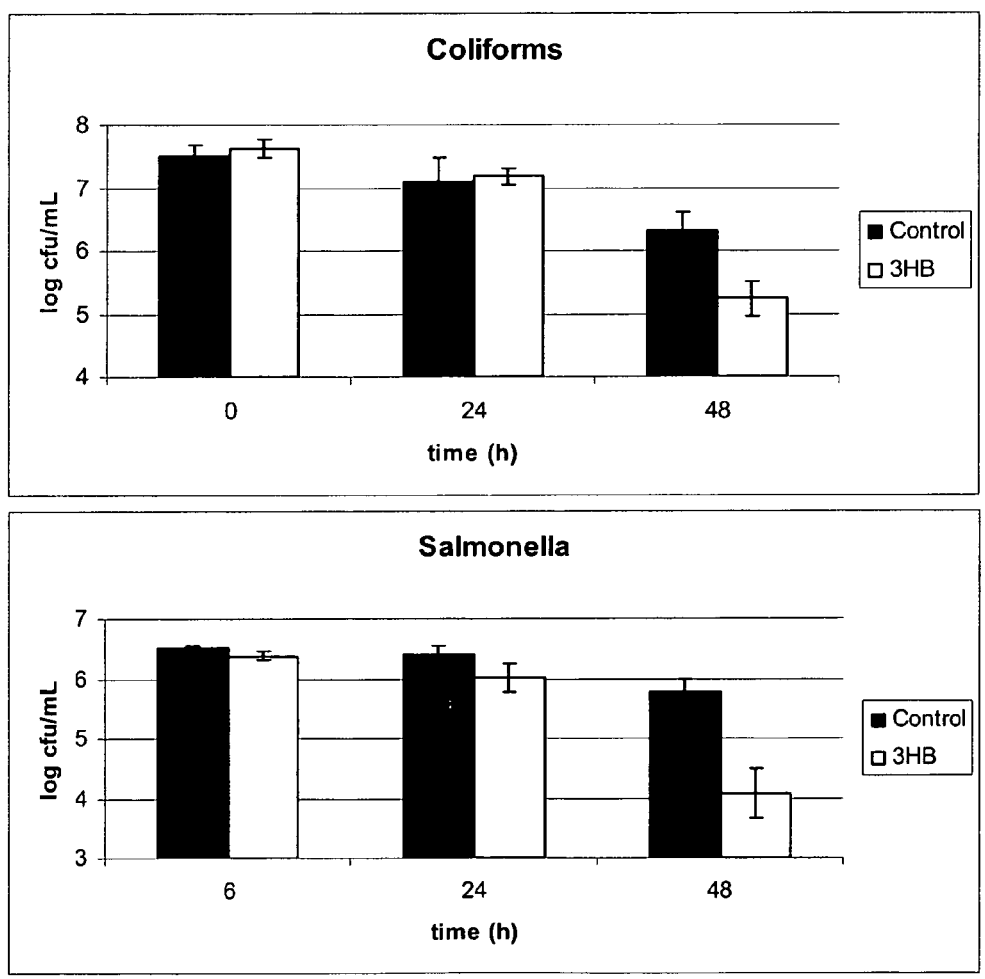
FIGS. 3, 4, and 5 show the effect of 3HB on the colon microbiota.
Figure 4:
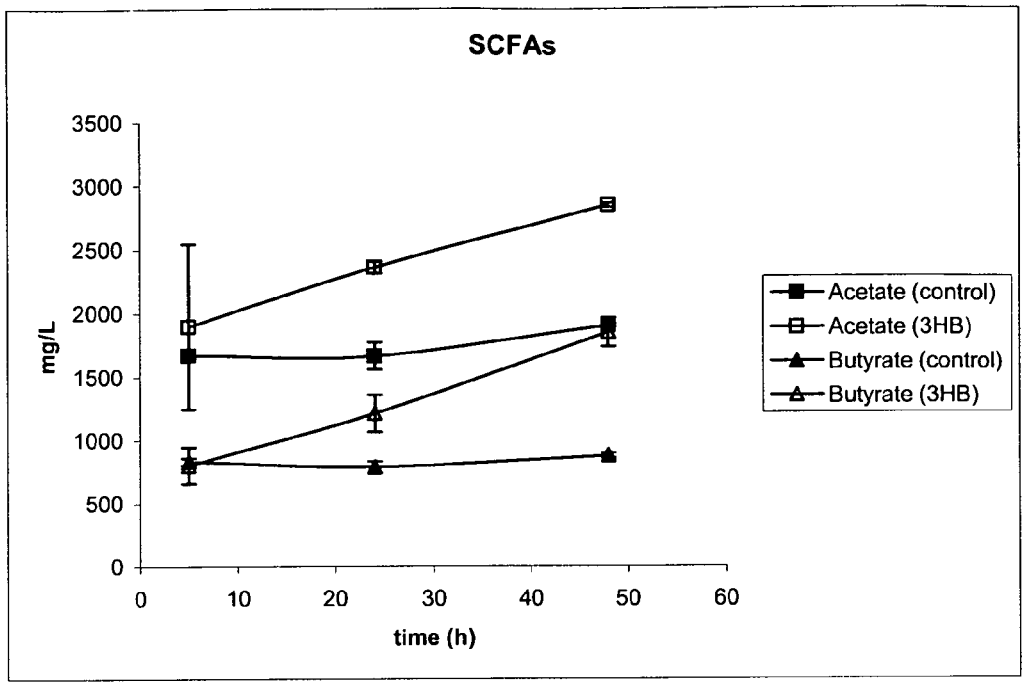
Figure 5:
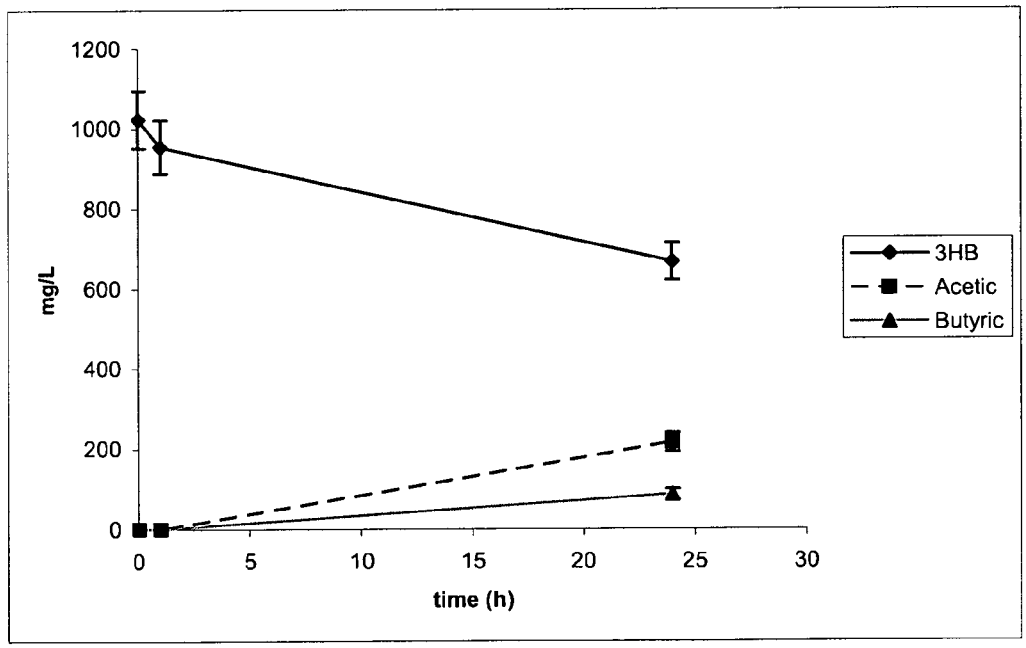

Supplementation of colon suspensions with 10 g/L of PHB resulted in a decrease of 1.7±0.3 and 1.1±0.28 log units for viable counts of *Salmonella* and coliforms, respectively, after 48 h of incubation in comparison with not supplemented samples (FIG. 3). Supplementation with PHB also resulted in a significant increase of butyrate and acetate levels of 110% and 50%, respectively, after 48 h of incubation (FIG. 4) suggesting a conversion of PHB to these SCFAs. Incubation of PHB in the presence of SHIME supernatant did not show any change in the SCFA profile (data not shown), indicating that transformation of PHB did not occur in the extracellular environment but it might be performed intracellularly by the intestinal microbiota. This was confirmed by incubating washed intestinal bacteria in mineral medium in the presence of PHB as the only carbon source. Under these conditions a decrease in PHB concentration corresponding with an equivalent increase of acetate and butyrate levels was observed (FIG. 5).

Effect of PHB on the Colon Microbiota

Commercial PHB was subjected to simulated stomach and small intestine digestion and release of degradation products (i.e. PHB, butyrate or crotonic acid) was determined by HPLC analysis. No traces of these compounds were found indicating that no chemical degradation of PHB occurred.

Biological degradation of PHB by the intestinal microbiota was studied by supplementing SHIME suspensions with 10 g/L of commercial PHB. Results did not show any significant change of the SCFAs profiles nor of the plate counts of selected microbial groups (coliforms, enterococci, lactobacilli or clostridia) with respect to the control samples without PHB (data not shown). Release of PHB degradation products was neither detected suggesting that no microbial degradation occurred. This assay was repeated using a PHB suspension previously subjected to sonication for 20 min at 4° C. using a Labsonic sonicator (Braum Biotech International, Melsungen, Germany) in order to improve bioavailability of PHB. Yet, no significant differences were observed with these experiments (data not shown).

Figure 6:
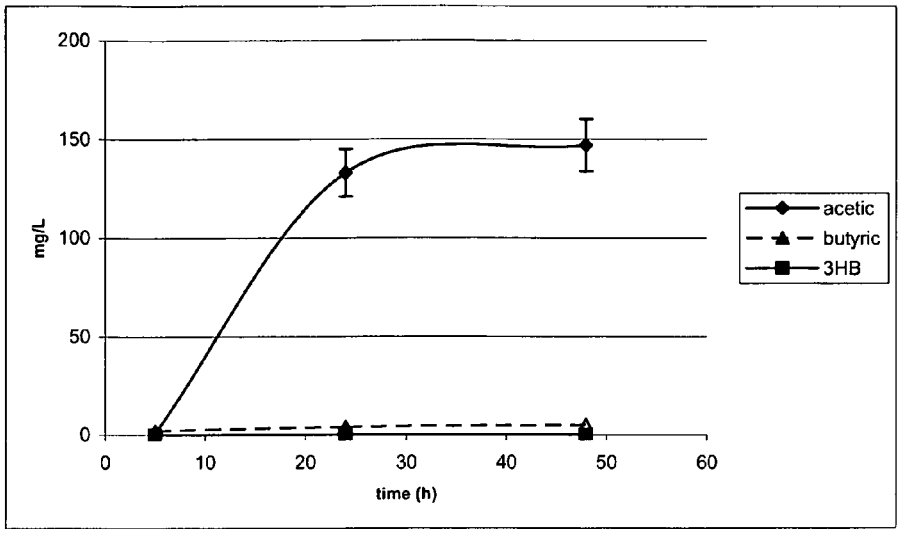
FIG. 6 is a graph showing the effect of PHB on the colon microbiota.

An alternative assay was performed using washed intestinal bacteria resuspended in mineral medium. In this form all additional carbon sources that might be present in the suspension were eliminated, PHB being the only carbon source available. Results (FIG. 6) showed a slight increase (143 mg/L) of the acetate levels and non-significant (5 mg/L) increase of butyric acid. No traces of PHB were observed.

Effect of Untreated PHB-Cells on the Colon Microbiota

Figure 7:
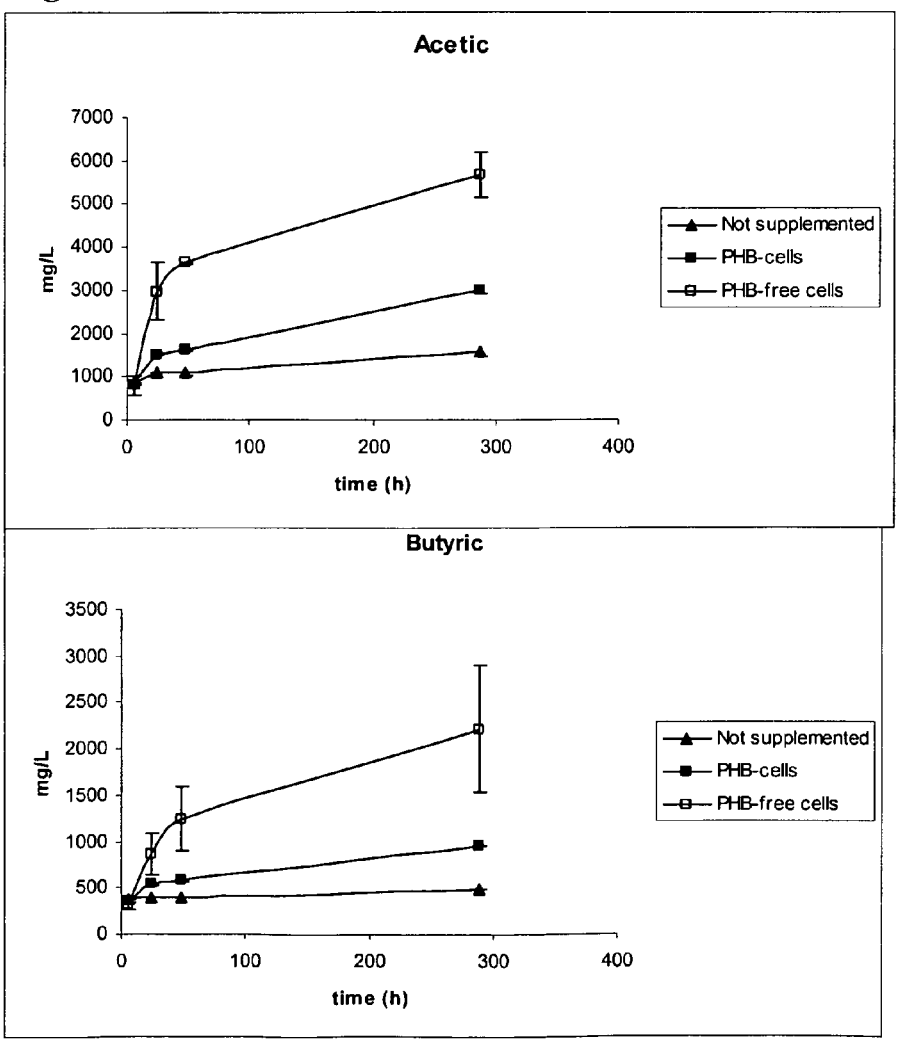
FIG. 7 is a series of graphs showing the effect of untreated PHB-cells on the colon microbiota.

A significantly lower production of SCFAs was observed in samples supplemented with lyophilized PHB-cells when compared with samples containing PHB-free cells (FIG. 7). No significant differences in microbial counts of selected groups (coliforms, enterococci, clostridia and lactobacilli) were observed (data not shown).

Hydrolysis of PHB-Cells

PHB-cells were subjected to different treatments in order to find the best conditions for PHB hydrolysis (Table 4).

TABLE 4

Hydrolysis products of PHB-cells after different acid/base treatments. All treatments performed with and acid/base concentration of 0.5 N.

| Treatment | PHB hydrolyzed (%) | Hydroxy-butyric acid (%) | Crotonic acid (%) | Hydroxy-valeric acid (%) |
|---|---|---|---|---|
| NaOH (4 h/100° C.) | 95.0 | 63.8 | 31.1 | 0.1 |
| NaOH (24 h/30° C.) | 8.6 | 5.7 | 2.8 | 0.0 |
| HCl (4 h/100° C.) | 0.4 | 0.1 | 0.0 | 0.0 |
| HCl (24 h/30° C.) | 0.0 | 0.0 | 0.0 | 0.0 |

Treatments at 30° C. or with HCl resulted in a very low degree of hydrolysis. Treatment with NaOH at 100° C. for 4 h resulted in hydrolysis of 95% of the total PHB content of the cell culture yielding 64% of 3HB, 31% of crotonic acid and traces of hydroxyvaleric acid.

Effect of Hydrolyzed PHB-Cells on the Ileum Microbiota

Similar initial counts for *Salmonella* were observed in the ileum (Table 5) and colon (FIG. 3) samples.

TABLE 5

Microbial counts and SCFAs levels after 48 h of incubation of simulated ileum samples in which part of the original feed was substituted by different amounts of hydrolyzed PHB-cells.

| PHB-cells (%) | Salmonella (log cfu/mL)[a] | Coliforms (log cfu/mL)[b] | Butyric acid (mg/L)[c] | Acetic acid (mg/L)[d] | 3HB (g/L) time 0 h | 3HB (g/L) time 48 h |
|---|---|---|---|---|---|---|
| 100 | <3 | <4 | 43.2 ± 6.1 | 254.3 ± 4.5 | 8.30 ± 0.22 | 8.22 ± 0.31 |
| 50 | <3 | <4 | 49.4 ± 11.1 | 269.6 ± 19.7 | 4.51 ± 0.69 | 4.43 ± 0.45 |
| 20 | 5.43 ± 0.07 | 8.12 ± 0.10 | 332.4 ± 13.4 | 3561.1 ± 46.1 | 1.62 ± 0.33 | 1.01 ± 0.05 |
| 10 | 5.61 ± 0.09 | 8.01 ± 0.05 | 106.6 ± 2.1 | 3379.8 ± 23.3 | 0.99 ± 0.07 | 0.42 ± 0.11 |
| 0 | 5.99 ± 0.14 | 7.56 ± 0.04 | 67.1 ± 6.2 | 2431.4 ± 36.1 | ND | ND |

[a]Initial Salmonella: 6.12 ± 0.04 log cfu/mL
[b]Initial coliforms: 6.90 ± 0.11 log cfu/mL.
[c]Initial butyric: 48 ± 7.1 mg/L
[d]Initial acetic: 257.4 ± 23.3 mg/L
ND = not detected In samples containing high doses of hydrolyzed PHB-cells, the growth of Salmonella and coliforms was strongly inhibited, showing a decrease in the number of viable counts of more than 3 log units. In fact, at this high supplementation levels no viable counts of any microbial group investigated, including clostridia, enterococci and lactobacilli (data not shown) were detected at the lowest dilution plated, which suggests a strong non-specific inhibitory effect from PHB. No changes on the levels of butyrate, acetate or PHB were observed in these samples, indicating a nearly total inactivation of the metabolic activity of the ileum microbiota. Supplementation of the feed with lower amounts of hydrolyzed PHB-cells gave rise to different results. Plate counts for Salmonella showed a decrease with respect to non-supplemented samples of 0.5 and 0.4 log units for 20 and 10% PHB-cells, respectively, indicating a slightly inhibitory effect. On the other hand, growth of coliforms increased with higher amounts of PHB-cells (0.6 and 0.5 log units for 20 and 10% PHB-cells respectively). Similar growth-promoter effect of hydrolyzed PHB-cells was observed in other microbial groups such as clostridia, enterococci or lactobacilli (data not shown). In both cases, supplementation with hydrolyzed PHB-cells resulted in higher levels of butyric and acetic acids. In samples containing 20% of PHB-cells a 5-fold increase of butyric acid was observed with respect to not supplemented samples whereas in the case of feed containing 10% of PHB-cells, the increase was 1.5-fold. The increase on acetic acid was similar for both samples, representing an average 1.5-fold increase respect to the control samples. A decrease on the initial levels of PHB was also observed, indicating that part of this acid was consumed and most likely converted into acetate and butyrate.

Example 8

3-Hydroxybutyrate and Hydrolyzed Poly-3-hydroxybutyrate-Inhibit Growth of Vibrio campbellii Experimental Approach Bacterial Strains and Growth Conditions Vibrio campbellii LMG21363 (=PN9801; Soto-Rodriguez et al., 2003) and Comamonas testosteroni LMG19554 (=12; Boon et al., 2000) were obtained from the BCCM/LMG Bacteria Collection (Ghent, Belgium). Vibrio campbellii LMG21363 and Aeromonas hydrophila LVS3 (Verschuere et al., 1999) were grown in Marine Broth (Difco Laboratories, Detroit, USA). Comamonas testosteroni LMG19554 was grown in LB medium. All strains were grown at 28° C. with shaking (100 min$^{-1}$).

The Effect of β-hydroxybutyrate and Butyrate on the Growth of Vibrio campbellii LMG21363

Vibrio campbellii LMG21363 was grown overnight in LB medium on a shaker at 28° C. Subsequently, the suspension was diluted 1:50 (v/v) in LB medium supplemented with butyrate (Sigma-Aldrich, Bornem, Belgium) or β-hydroxybutyrate (Sigma-Aldrich, Bornem, Belgium). For each compound, three solutions were made with the following concentrations: 25, 50 and 100 mM. LB medium without supplements was used as a control. The pH of all solutions was set at 6, 7 or 8. After inoculation, the suspensions were incubated at 28° C. in a static mode. Growth was monitored by measuring the optical density (OD600) during 20 h. Each treatment was performed in triplicate.

Extracellular PHB Depolymerase Assay

Extracellular PHB depolymerase production was assayed in a qualitative way by streaking strains on solid medium containing PHB powder as the sole C-source. Extracellular PHB depolymerase hydrolyses the PHB polymer into water-soluble products and therefore, strains that produce extracellular PHB depolymerase can be recognised by the appearance of transparent clearing zones around the colonies (Jendrossek and Handrick, 2002). The medium used in the experiments contained 500 mg I-1 PHB Powder (average diameter 30 µm; Goodfellow, Huntingdon, UK), 1 g I-1 NH$_4$Cl, 1 g l$^{-1}$ KNO$_3$, 5 g l$^{-1}$ artificial seasalt (Aquarium Systems Inc., Sarrebourg, France) and 15 g l$^{-1}$ agar. The plates were incubated for up to 4 days at 28° C. and examined daily for the presence of a clearing zone around the colonies.

Axenic Hatching of Artemia franciscana

All challenge tests were performed with high quality hatching cysts of Artemia franciscana (EG® Type, batch 6940, INVE Aquaculture, Baasrode, Belgium). Two hundred mg of cysts were hydrated in 18 ml of tap water during 1 h. Sterile cysts and nauplii were obtained via decapsulation, adapted from the protocol described by Marques et al. (2004). Briefly, 660 µl of NaOH (32%) and 10 ml of NaOCl (50%) were added to the hydrated cyst suspension. The decapsulation was stopped after 2 min by adding 14 ml of Na$_2$S$_2$O$_3$ (10 gl$^{-1}$). During the reaction, 0.22 µm filtered aeration was provided. The decapsulated cysts were washed with autoclaved artificial seawater containing 35 g l$^{-1}$ of Instant Ocean synthetic sea salt (Aquarium Systems Inc., Sarrebourg, France).

The cysts were resuspended in a 50 ml tube containing 30 ml of filtered and autoclaved artificial seawater and hatched for 24 h on a rotor (4 min$^{-1}$) at 28° C. with constant illumination (approximately 2000 lux).

Preparation of the Inocula for In Vivo Challenge Tests

*Vibrio campbellii* LMG21363 was stored in 40% glycerol at −80° C. Ten μl of this stored culture was inoculated into fresh Marine Broth (Difco Laboratories, Detroit, USA) and incubated overnight at 28° C. under constant agitation (100 min-1). The grown cultures of *Vibrio campbellii* were washed in autoclaved artificial seawater and the suspensions were diluted to an OD600 of approximately 0.1. 20 μl of the diluted suspensions was inoculated into the *Artemia* culture water.

*Aeromonas hydrophila* LVS3 was used as feed for the nauplii (Defoirdt et al., 2005). The strain was grown overnight on Marine Agar (Difco Laboratories, Detroit, USA), suspended in sterile artificial seawater, diluted to an OD600 of approximately 1 and autoclaved. 300 μl of the autoclaved suspension was added to the *Artemia* culture water.

For the experiment with PHB (Commercial PHB from Goodfellow, Huntingdon, UK, final conc. 2.5 g/L) granules, *Comamonas testosteroni* LMG19554 was grown for 24 h in Marine Broth (Difco Laboratories, Detroit, USA), washed in sterile artificial seawater and diluted to an OD600 of approximately 1. 200 μl of the diluted suspension was added to the *Artemia* culture water.

In Vivo Challenge Tests

Challenge tests were performed as described by Defoirdt et al. (2005), with slight modifications. Briefly, after hatching, groups of 20 nauplii were transferred to new sterile 50 ml tubes that contained 20 ml of filtered and autoclaved artificial seawater. The tubes were inoculated with *Vibrio campbellii* LMG21363 (except for the control, where no pathogen was added) and fed with LVS3. For the experiment with fatty acids, the fatty acids were dissolved in artificial seawater at different concentrations (25, 50 and 100 mM). The pH of the solutions was brought back to 7 and the solutions were filter-sterilised over a 0.22 μm filter (Millipore, Bedford, USA). After feeding and the addition of the appropriate chemical and/or bacteria, the falcon tubes were put back on the rotor and kept at 28° C. The survival of *Artemia* was scored 2 days after the addition of the pathogen. All manipulations were done under a laminar flow hood in order to maintain sterility of the cysts and nauplii. Each treatment was done in triplicate.

Results

The effect of β-hydroxybutyrate on Growth of *Vibrio campbellii* LMG21363

The short-chain fatty acid β-hydroxybutyrate was tested for its ability to inhibit the growth of the pathogenic isolate *Vibrio campbellii* LMG21363. At pH 6, the growth of *Vibrio campbellii* was strongly inhibited if the medium was supplemented with 100 mM β-hydroxybutyrate. The growth of *Vibrio campbellii* was not completely inhibited in the presence of lower concentrations of the fatty acid. However, the growth rate was clearly lower than for the control and inversely related to the concentration of β-hydroxybutyrate. Butyrate was used as a reference fatty acid since its growth-inhibitory effect is well documented and since it has the same pKa value as β-hydroxybutyrate. The inhibition of growth by butyrate was more pronounced than by β-hydroxybutyrate. At pH 6, the growth of the pathogen was completely inhibited even for the lowest concentration tested. The growth inhibitory effect of both fatty acids was clearly pH-dependent since at pH 7, growth of the pathogen was only inhibited in medium supplemented with the highest concentration of butyrate and at pH 8, no inhibition was observed.

The Effect of β-hydroxybutyrate on the Survival of *Artemia nauplii* Infected with *Vibrio campbellii* LMG21363

In a first in vivo challenge test, the effect of the addition of β-hydroxybutyrate on the survival of *Artemia nauplii* infected with the pathogenic isolate *Vibrio campbellii* LMG21363 was investigated. β-hydroxybutyrate significantly enhanced the survival of the infected nauplii when added at a concentration of 100 mM as it is shown in Table 6.

TABLE 6

Percentage survival of *Artemia nauplii* (mean ± standard error of three replicates) after 2 days challenge with *Vibrio campbellii* LMG21363. β-hydroxybutyrate or butyrate were added at 25 or 100 mM to the *Artemia* culture water at the start of the experiment.

| Treatment | Survival (%) |
| --- | --- |
| Control | 80 ± 3 |
| LMG21363 | 12 ± 2 |
| LMG21363 + β-hydroxybutyrate (25 mM) | 38 ± 15 |
| LMG21363 + β-hydroxybutyrate (100 mM) | 40 ± 3* |
| LMG21363 + butyrate (25 mM) | 48 ± 2* |
| LMG21363 + butyrate (100 mM) | 50 ± 5* |

*Significant difference in survival with infected *nauplii* without the addition of fatty acid (P < 0.01)

The survival of the nauplii with 25 mM β-hydroxybutyrate was also higher than the survival of infected nauplii without the fatty acid. However, the difference was not significant due to a high variation. Butyrate, which was again used as a reference, significantly enhanced the survival of the infected nauplii for both concentrations tested. Both fatty acids had no effect on the survival of uninfected nauplii at the highest concentration tested (data not shown).

Depolymerisation of PHB Granules

*Comamonas testosteroni* has been reported before to be able to produce extracellular PHB depolymerase. Consequently, different *Comamonas testosteroni* strains were screened for PHB depolymerisation by streaking them onto agar containing PHB granules as the sole C-source and checking for the formation of a clearing zone. One of the strains, *Comamonas testosteroni* LMG19554, showed excellent PHB depolymerase activity since a clearing zone was present around the colonies already after 1 day of incubation. After 2 days of incubation, a large clearing zone with complete clearing of the medium was observed. Extracellular PHB depolymerase production was also assessed for *Vibrio campbellii* LMG21363. However, no clearing of the medium could be observed.

The Effect of In Vivo Depolymerisation of PHB on the Survival of *Artemia nauplii* Infected with *Vibrio campbellii* LMG21363

A further in vivo experiment aimed at testing whether the addition of PHB granules would result in a protection from the pathogenic *Vibrio campbellii*. The survival of the infected *Artemia nauplii* was found to be proportional to the concentration of PHB added to the culture water as shown in Table 7.

TABLE 7

Percentage survival of *Artemia nauplii* (mean ± standard error of three replicates) after 2 days challenge with *Vibrio campbellii* LMG21363. PHB particles were added to the culture water either at the start of the experiment (with or without the extracellular PHB depolymerase producing strain *Comamonas* testosterone LMG 19554) or after 1 day.

| Treatment | Survival (%) without Comamonas | Survival (%) with Comamonas |
|---|---|---|
| Control | 87 ± 3 | NT |
| LMG21363 | 17 ± 2 | 18 ± 2 |
| LMG21363 + PHB (10 mg I-1; start) | 22 ± 4 | 20 ± 5 |
| LMG21363 + PHB (100 mg I-1; start) | 40 ± 3* | 62 ± 4* |
| LMG21363 + PHB (1000 mg I-1; start) | 90 ± 3* | 92 ± 3* |
| LMG21363 + PHB (10 mg I-1; day 1) | 18 ± 7 | NT |
| LMG21363 + PHB (100 mg I-1; day 1) | 38 ± 2* | NT |
| LMG21363 + PHB (1000 mg I-1; day 1) | 60 ± 6* | NT |

*Significant difference in survival with infected nauplii without the addition of PHB ($P < 0.01$)
NT: Not Tested The addition of PHB significantly enhanced the survival of the infected nauplii when added at 100 mg l$^{-1}$ and 1000 mg l$^{-1}$ ($P<0.01$). The PHB depolymerising strain *Comamonas testosteroni* LMG19554 significantly improved the performance of the PHB granules at 100 mg l$^{-1}$ ($P<0.05$). The strain had no effect on the survival of infected *nauplii* in the absence of PHB.

If the PHB granules were added together with the pathogen, a complete protection (no significant difference in survival with uninfected nauplii) was observed at the highest concentration tested, with no difference between tubes with and tubes without *Comamonas testosteroni* LMG19554. If the granules were added 1 day after the addition of the pathogen, a similar but less pronounced effect was noticed. The addition of PHB significantly enhanced the survival of the infected nauplii when added at 100 mg l$^{-1}$ and 1000 mg l$^{-1}$ ($P<0.01$) as was the case if the granules were added together with *Vibrio campbellii* LMG21363. However, in this case, there was still significant mortality in infected *Artemia* treated with 1000 mg l$^{-1}$ PHB ($P<0.01$).

Example 9

Effect of a PHB Accumulating Bacteria Inhibit on the Growth of *Vibrio campbellii*

Experimental Approach

Enrichment of PHB-Accumulating Bacteria

*Ralstonia eutropha* (ATCC 17699) used as PHE-accumulating bacteria were enriched in a sequencing batch reactor inoculated with activated sludge kom a laboratory scale polyphosphate-accumulating reactor as described by Serafim et al. Optimization of polyhydroxybutyrate production by mixed cultures submitted to aerobic dynamic feeding conditions, Biotechnol. Bioeng. 87, 145-160, 2004.

Isolation of Pure Cultures of PHB Accumulating Bacteria

Microbiological isolation of PHB-accumulating bacteria was carried out by a spread-plate method previously described (Spiekermann et al 1999), with slight modifications. To prepare solid medium for isolation, 15 g of Technical Agar (Difco, Detroit, USA) was added to 1 l of the mineral salts medium used in the sequencing batch reactor. Subsequently, 0.002% (v/v) of a solution of 0.25 mg Nile blue A (Sigma, St., Louis, USA) per ml DMSO was added to the sterilized medium to give a final concentration of 0.5 µg dye (ml medium)$^{-1}$. The agar plates were exposed to ultraviolet light (312 nm) after appropriate cultivation period to detect for PUB accumulation in the grown colonies.

The isolates were grown fcr 24 h in LB-medium at 28° C. with shaking After the incubation, the cells were centrifuged (8 min 5000 rpm) and resuspended in the mineral salts medium used in the sequencing batch reactor the cultures were areated and samples were taken every hour in order to determine the PHB content Determination of the PHB Content PHB concentrations were measured with a Di200 gas chromatograph (Shimadzu, 's-Hertogenbosch, The Netherlands) following the procedure described by Oehmen et al. (2005). The gas chromatograph was equipped with a capillary free fatty acid packed column [EC.-1000 Econo-Cap column (Altech, Laarne, Belgium), 25 m×0.53 mm; film thickness 1.2 µm], a flame ionization detector and a Delsi Nermag 31 integrator (Thermo Separation Products, Wilrijk, Belgium). Nitrogen was used as the carrier gas at a flow rate of 3 ml min$^{-1}$.

Preparation of the Inocula for In Vivo Challenge Tests

*Vibrio campbellii* LMG21363 was stored in 40% glycerol at −80° C. Ten µl of this stored culture was inoculated into fresh Marine Broth (Difco Laboratories. Detroit, USA) and incubated for 24 h at 28° C. under constant agitation (100 min). The grown cultures of *Vibrio campbellii* were washed in filtered and autoclaved artificial seawater and added to the *Artemia* culture water at approx. 10$^5$ CFU ml$^{-1}$.

*Aeromonas hydrophila* LVS3 (Verschuere et al, 1999) was used as feed for the nauplii (Defoirdt et al., 2005). The strain was grown overnight on Marine Agar (Difco Laboratories, Detroit, USA), suspended in sterile artificial seawater, autoclaved and added to the *Artemia* culture water at approx. 10$^7$ cells ml$^{-1}$.

In Vivo Challenge Tests

Challenge tests were performed as described by Defoirdt et al. (2005), with slight modifications. Briefly, after hatching, groups of 20 nauplii were transferred to new sterile 50 ml tubes that contained 20 ml of filtered and autoclaved artificial seawater. The tubes were inoculated with *Vibdo campbellii* LMG21363 (except for the control, where no pathogen was added) and fed with LVS3. PWB accumulating bacteria were added to the *Artemia* culture water at approximately 10$^7$ CFU ml$^{-1}$.

After feeding and the addition of the appropriate bacteria, the falcon tubes were put back on the rotor and kept at 28° C. The survival of *Artemia* was scored 2 days after the addition of the pathogen. All manipulations were done under a laminar flow hood in order to maintain sterility of the cysts and nauplii. Each treatment was done in triplicate.

Results

The Effect of the PHB-Accumulating Enrichment Culture on the Survival of Infected *Artemia*

The effect of the PHB-accumulating enrichment culture on the survival of *Artemia nauplii* infected with the pathogenic isolate *Vibrio campbellii* LMG2363 is illustrated in Table 8. The biomass was growing as aggregates in the sequencing batch reactor and therefore, the culture was subjected to different treatments that aimed at making the PHB more available for *Artemia*. If it was subjected to 3 cycles of freezing and thawing prior to addition to the culture water, the addition of the enrichment culture (containing 15% PHB on VSS or more) significantly enhanced the survival of the infected nauplii. Adding the culture untreated or after pasteurization (30 min 60%) had no effect on the survival of the infected *Artemia*.

TABLE 8

Percentage survival of *Artemia nauplii* (mean standard error of three replicates) after 2 days challenge with *Vibrio campbellii* LMG21363. The PHB-accumulating enrichment culture was added to the *Artemia* culture water either untreated or after pasteurization or freezing and thawing. The enrichment culture was sampled at three time points and contained 2, 15 or 25% PHB on VSS.

| Treatment | Survival (%) |
|---|---|
| Control | 83 ± 2 |
| LMG21363 | 10 ± 3 |
| LMG21363 + Culture (25% PHB, untreated) | 12 ± 4 |
| LMG21363 + Culture (25% PHB, pasteurized) | 18 ± 3 |
| LMG21363 + Culture (25% PHB, freezing and thawing) | 67 ± 7* |
| LMG21363 + Culture (15% PHB, freezing and thawing) | 43 ± 2* |
| LMG21363 + Culture (2% PHB, freezing and thawing) | 7 ± 2 |

*Survival significantly different from the treatment with pathogen and without PHB-accumulating bacteria (P < 0.01)

The enrichment culture was sampled after 2 and 6 hours during PHB enrichment: and after 1 day of starvation. By doing this way, the same enrichment culture was obtained with different PHB concentrations (25, 15 and 2% of the VSS, respectively). Importantly, the concentration of VSS was the same in all three cases. The survival of the infected *nauplii* was clearly proportional to the PHB content of the enrichment culture (Table 8).

REFERENCES

Jendrossek and Handrick, Microbial degradation of polyhydroxalkanoates, Annu. Rev. Microbiol 567, 403-432, 2002

Verschuere, Rombaut, Huys, Dhont, Sorgeloos, and Verstraete, Microbial control of the culture of *Artemia* juveniles through preeptive colonization by selected bacterial strains, Appl. Environ. Microbiol. 65, 2527-2533, 1999

Boon, N, Goris, J, De Vos, P, Verstraete, W and Top, E M (2000), Bioaugmentation of activated sludge by an indigenous 3-chloroaniline-degrading *Cornamonas teslostefoni* strain, 12gfp Appl Environ Microbial 8% 2906-2913

Defoirdt, T., Bossier, P, Sorgeloos, P. and Verstraete, W. (2005) The impact of mutations in the quorum sensing systems of *Aeromonas* hydrophila, Vibp-in zngui/larum and b"ibro harveyi on their virulence fawards gnotobiotically cuitured, Ademia franciscans Envim Microbial 7, ?239-I 249

Marques, A, Francois, J. M., Dhont, J, Bossier, P, and Sorgeloos, P. (2004), Influence of yeast quality on performance of gnotobiotically grown *Artemia*. J Exp, Mar Biol Ecol 330, 247-264, Oehmen, A, Keller-iehmann, 8, Zeng, R J. Yuan, Z G and Keller, E (2005), Optimisation of poly-beta-hydroxyalkanoate analysis using gas chromatography for enhanced biological phosphorus removal systems J GhromatogrA 1070, 133-1363

Serafim, S, Lemos, P. C, Oliveira, R. and Reis, M A M. (2004) Optimization of polyhydroxybutyrate production by mixed cultures submitted to aerobic dynamic feeding conditions. Biotechnol Bioeng 87, 145-160

Spiekermann, P., Rehrn, BFI A, Kalscheuer, R, Baumeister, D. and SteinbUchei, A, (1999), A sensitive, viabre-colony staining method using Nile red for direct screening of bacteria that accumulate polyhydroxyalkanoic acids and other lipid storage compounds. Arch Microbiol 271, 73-80

Soto-Rodriguez et al., Virulence of luminous vibrios to *Artemia franciscana nauplii*, Dis Aquat Org 53, 231-240, 2003

De Boever, P., Deplancke, B., and Verstraete, W., 2000, Fermentation by gut microbiota cultured in a simulator of the human intestinal microbial ecosystem is improved by supplementing a soygerm powder. J Nutr 130: 2599-2606".

The invention claimed is:

1. A feed or feed additive comprising, as gut flora modulating active ingredients:
    poly-3-hydroxybutyrate (PHB) or a microbial strain capable of producing PHB, and
    at least one depolymerase or a strain capable of expressing such a depolymerase.

2. A feed or feed additive comprising, as gut flora modulating active ingredients:
    poly-3-hydroxybutyrate (PHB) or a microbial strain capable of producing PHB, and
    at least one depolymerase or a microbial strain capable of producing such a depolymerase, wherein said depolymerase is selected from the group consisting of an extracellular PHB depolymerase enzyme, an extracellular endo-type hydrolase enzyme, an extracellular oligomer hydrolase enzyme, and an intracellular PHB depolymerase enzyme.

3. The feed or feed additive according to claim 2, wherein said strain capable of producing a depolymerase is *Comamonas* testosterone (LMG19554).

4. The feed or feed additive according to claim 1, further comprising:
    (a) at least one fat-soluble vitamin,
    (b) at least one water-soluble vitamin,
    (c) at least one trace mineral, and/or
    (d) at least one macro mineral.

5. A combination of at least two compositions for use in feed, drinking water or feed additives said combination comprising:
    a first composition comprising a poly-3-hydroxybutyrate or a microbial strain capable of producing poly-3-hydroxybutyrate; and
    a second composition comprising at least one depolymerase or a strain expressing such a depolymerase.

6. A method of treating a microbial infection caused by *Vibrio campbelli* in an animal, comprising the administration of an antimicrobial composition comprising an effective amount of 3-hydroxybutyrate and/or poly-3-hydroxybutyrate to said animal.

7. The feed or feed additive according to claim 2, further comprising:
    (a) at least one fat-soluble vitamin,
    (b) at least one water-soluble vitamin,
    (c) at least one trace mineral, and/or
    (d) at least one macro mineral.

8. The feed or feed additive according to claim 3, further comprising:
    (a) at least one fat-soluble vitamin,
    (b) at least one water-soluble vitamin,
    (c) at least one trace mineral, and/or
    (d) at least one macro mineral.

9. The feed or feed additive according to claim 1, wherein said microbial strain capable of producing PHB is a *Ralstonia* or *Rhodobacter* strain.

10. The feed or feed additive according to claim 2, wherein said microbial strain capable of producing PHB is a *Ralstonia* or *Rhodobacter* strain.

11. The feed or feed additive according to claim 1, wherein said microbial strain is present in the form of a dry biomass containing 100 to 500 g PHB/kg biomass.

12. The feed or feed additive according to claim 2, wherein said microbial strain is present in the form of a dry biomass containing 100 to 500 g PHB/kg biomass.

13. The feed according to claim 1, being in the form of an animal feed or drinking water composition comprising:
   (a) PHB and a PHB depolymerase, and
   (b) a crude protein content of 50 to 800 g/kg feed.

14. The feed according to claim 2, being in the form of an animal feed or drinking water composition comprising:
   (a) PHB and a PHB depolymerase, and
   (b) a crude protein content of 50 to 800 g/kg feed.

* * * * *

UNITED STATES PATENT AND TRADEMARK OFFICE
CERTIFICATE OF CORRECTION

| | | |
|---|---|---|
| PATENT NO. | : 8,603,518 B2 | Page 1 of 1 |
| APPLICATION NO. | : 12/299182 | |
| DATED | : December 10, 2013 | |
| INVENTOR(S) | : Boon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1437 days.

Signed and Sealed this
Seventh Day of April, 2015

Michelle K. Lee
*Director of the United States Patent and Trademark Office*